US012752052B2

(12) United States Patent
Schøndorff et al.

(10) Patent No.: US 12,752,052 B2
(45) Date of Patent: *Oct. 6, 2026

(54) CANNULA AND INFUSION DEVICES

(71) Applicant: UnoMedical A/S, Birkerød (DK)

(72) Inventors: Pernelle Kruse Schøndorff, Tune (DK); Julie Theander, Oelstykke (DK); Rasmus Boje Vendelbo Juliussen, Søborg (DK)

(73) Assignee: Unomedical A/S, Lejre (DK)

( * ) Notice: Subject to any disclaimer, the term of this patent is extended or adjusted under 35 U.S.C. 154(b) by 1098 days.

This patent is subject to a terminal disclaimer.

(21) Appl. No.: 17/746,311

(22) Filed: May 17, 2022

(65) Prior Publication Data

US 2022/0296810 A1 Sep. 22, 2022

Related U.S. Application Data

(63) Continuation of application No. 16/071,428, filed as application No. PCT/IB2017/000081 on Jan. 19, 2017, now Pat. No. 11,357,912.

(Continued)

(51) Int. Cl.
*A61B 17/34* (2006.01)
*A61M 5/142* (2006.01)
(Continued)

(52) U.S. Cl.
CPC ......... *A61M 5/158* (2013.01); *A61B 17/3417* (2013.01); *A61B 17/3421* (2013.01);
(Continued)

(58) Field of Classification Search
CPC .............. A61M 5/3291; A61M 25/007; A61M 25/0015; A61M 25/0068; A61B 17/3417; A61B 2017/3454
See application file for complete search history.

(56) References Cited

U.S. PATENT DOCUMENTS 1,719,428 A * 7/1929 Friedman ............ A61M 3/0291 604/105
2,649,092 A * 8/1953 Wallace ................ A61M 25/04 604/105
(Continued)

FOREIGN PATENT DOCUMENTS

WO 2006118804 A1 11/2006
WO 2010051079 A2 5/2010
(Continued)

OTHER PUBLICATIONS

Shannon, Geoff, Fine Laser Cutting for Medical Components, Sep. 24, 2014 (Year: 2014).*
(Continued)

*Primary Examiner* — William R Carpenter
*Assistant Examiner* — Robert F Allen
(74) *Attorney, Agent, or Firm* — TAFT STETTINIUS HOLLISTER LLP; Ryan O. White; Derek B. Lavender

(57) ABSTRACT

An infusion device according to certain embodiments is provided for subcutaneous delivery of a therapeutic agent to a patient. The infusion device generally includes a cannula and a hub part. The cannula includes a tubular body member including a tubular wall at least partly enclosing a longitudinally-extending internal bore. A distal portion of the tubular body member includes a distal tip end including at least one tip opening. The tubular wall includes at least two weakened portions capable of allowing the cannula to flex in an area including the weakened portions when the cannula is exposed to a compression force and/or an increased internal pressure. The hub part is configured to be fastened onto the patient's skin via a mounting pad.

10 Claims, 17 Drawing Sheets

Related U.S. Application Data

(60) Provisional application No. 62/280,345, filed on Jan. 19, 2016.

(51) Int. Cl.
*A61M 5/158* (2006.01)
*A61M 5/32* (2006.01)
*A61M 25/00* (2006.01)
*A61M 25/09* (2006.01)

(52) U.S. Cl.
CPC ...... *A61M 5/14248* (2013.01); *A61M 5/3291* (2013.01); *A61M 25/00* (2013.01); *A61M 25/0043* (2013.01); *A61M 25/0068* (2013.01); *A61B 2017/3454* (2013.01); *A61M 25/0015* (2013.01); *A61M 25/007* (2013.01); *A61M 2025/09175* (2013.01)

(56) References Cited

U.S. PATENT DOCUMENTS 3,799,172 A * 3/1974 Szpur .................... A61M 25/04 604/105
4,154,242 A * 5/1979 Termanini ............. A61M 25/04 604/105
4,549,879 A * 10/1985 Groshong ......... A61M 25/0075 604/9
4,671,796 A * 6/1987 Groshong ......... A61M 25/0075 604/170.01
4,701,166 A * 10/1987 Groshong ......... A61M 25/0075 604/8
4,801,297 A * 1/1989 Mueller ............ A61M 25/0068 604/247
5,193,533 A * 3/1993 Body .................... A61M 25/04 128/207.14
5,425,723 A 6/1995 Wang
5,533,986 A * 7/1996 Mottola ............ A61M 25/0075 604/264
5,702,365 A * 12/1997 King ..................... A61M 29/02 604/105
5,807,349 A 9/1998 Person et al.
5,817,072 A * 10/1998 Lampropoulos ...... A61M 39/06 604/264
5,857,464 A * 1/1999 Desai .................. A61M 25/007 604/246
6,261,272 B1 7/2001 Gross et al.
6,533,763 B1 3/2003 Schneiter
6,569,145 B1 * 5/2003 Shmulewitz ..... A61B 17/12022 604/509
6,701,180 B1 * 3/2004 Desai .................. A61M 25/007 604/105
7,264,609 B2 * 9/2007 Hakky .............. A61M 25/0017 604/908
8,267,891 B2 * 9/2012 Dimalanta .......... A61F 9/00736 604/167.04
10,071,210 B2 9/2018 Gray
10,292,641 B2 5/2019 Bureau et al.
10,293,101 B2 5/2019 Brewer et al.
10,369,274 B2 8/2019 O'Connor et al.
10,369,289 B2 8/2019 Cabin et al.
10,376,638 B2 8/2019 Levesque et al.
10,413,661 B2 9/2019 Kamen et al.
10,432,403 B2 10/2019 Moskal
10,434,245 B2 10/2019 Yodfat et al.
10,434,247 B2 10/2019 Cole et al.
10,434,253 B2 10/2019 DiPerna et al.
10,434,285 B2 10/2019 Schoonmaker et al.
10,438,696 B2 10/2019 Shapley et al.
10,441,356 B2 10/2019 Zarins et al.
10,441,713 B1 10/2019 Feldman et al.
10,441,718 B2 10/2019 Tchao et al.
10,441,723 B2 10/2019 Nazzaro
10,441,775 B2 10/2019 Schriver et al.
10,449,290 B2 10/2019 Shapley et al.
10,449,291 B2 10/2019 Hadian et al.
10,449,306 B2 10/2019 Grover et al.
10,463,785 B2 11/2019 Dewey
10,463,791 B2 11/2019 Shergold et al.
10,471,203 B2 11/2019 Chappel et al.
10,471,206 B2 11/2019 Dittrich
10,478,550 B2 11/2019 Hadvary et al.
10,478,552 B2 11/2019 Cronenberg et al.
10,478,554 B2 11/2019 Bazargan et al.
10,478,555 B2 11/2019 Radojicic
10,483,000 B2 11/2019 Saint et al.
10,485,923 B2 11/2019 Schiendzielorz
10,485,926 B2 11/2019 Vanderveen et al.
10,485,937 B2 11/2019 Yodfat et al.
10,489,617 B2 11/2019 Salem et al.
10,493,201 B2 12/2019 Cole et al.
10,493,202 B2 12/2019 Hayter
10,493,203 B2 12/2019 Yodfat et al.
10,500,352 B2 12/2019 Grant et al.
10,507,316 B2 12/2019 Fielder et al.
10,512,724 B2 12/2019 Renstad et al.
10,525,193 B2 1/2020 Schaudema
10,525,247 B2 1/2020 Bellrichard et al.
10,532,150 B2 1/2020 Bazargan et al.
10,532,151 B2 1/2020 Wei
10,532,155 B2 1/2020 Xchiendzielorz
10,532,159 B2 1/2020 Tornsten et al.
10,532,835 B2 1/2020 Chong et al.
10,537,681 B2 1/2020 Tan-Malecki et al.
10,539,481 B2 1/2020 Plahey et al.
10,542,936 B2 1/2020 Goldberg et al.
10,549,029 B2 2/2020 Agard et al.
10,549,033 B2 2/2020 Shimizu
10,549,034 B2 2/2020 Eggert et al.
10,549,036 B2 2/2020 Starkweather et al.
10,549,079 B2 2/2020 Burton et al.
10,556,059 B2 2/2020 Cross et al.
10,556,063 B2 2/2020 Murphy, Jr. et al.
10,561,785 B2 2/2020 Roy et al.
10,561,788 B2 2/2020 Roy
10,561,789 B2 2/2020 Mastrototaro et al.
10,561,826 B2 2/2020 Amano et al.
10,561,831 B2 2/2020 Kato
10,569,011 B2 2/2020 Dilanni et al.
10,569,012 B2 2/2020 Schabbach et al.
10,569,014 B2 2/2020 Hanson et al.
10,576,199 B2 3/2020 Sealfon et al.
10,576,203 B2 3/2020 Arnon et al.
10,576,204 B2 3/2020 Estes et al.
10,583,241 B2 3/2020 Wu et al.
10,583,247 B2 3/2020 Mandro
10,589,023 B2 3/2020 Cindrich et al.
10,589,028 B2 3/2020 Cabiri et al.
10,596,317 B2 3/2020 Nakanishi
10,596,362 B2 3/2020 Fielder et al.
10,610,638 B2 4/2020 Cabin et al.
10,610,639 B2 4/2020 Cabiri et al.
10,610,644 B2 4/2020 Mazlish et al.
10,617,617 B1 4/2020 Hwang et al.
10,617,820 B2 4/2020 O'Connor et al.
10,625,016 B2 4/2020 Amon et al.
10,625,017 B2 4/2020 Searle et al.
10,625,018 B2 4/2020 Destafano et al.
10,632,248 B2 4/2020 Stefanov et al.
10,632,249 B2 4/2020 Marbet et al.
10,632,253 B2 4/2020 Uchiyama et al.
10,632,256 B2 4/2020 Sasaki
10,632,257 B2 4/2020 Estes et al.
10,635,784 B2 4/2020 Rubalcaba, Jr. et al.
10,639,418 B2 5/2020 Kamen et al.
10,639,661 B2 5/2020 Fontana
10,646,643 B2 5/2020 Cabiri et al.
10,646,652 B2 5/2020 McCullough et al.
10,646,653 B2 5/2020 Despa et al.
10,653,828 B2 5/2020 Brown et al.
10,653,829 B2 5/2020 Barchen et al.
10,653,833 B2 5/2020 Kamen et al.
10,653,835 B2 5/2020 Dobbies et al.

(56) References Cited

U.S. PATENT DOCUMENTS 10,653,846 B2 5/2020 Weibel et al.
10,661,006 B2 5/2020 Antonio et al.
10,661,007 B2 5/2020 Estes et al.
10,661,008 B2 5/2020 Brewer et al.
10,661,067 B2 5/2020 Kodama
10,668,210 B2 6/2020 Kamen et al.
10,668,213 B2 6/2020 Cabiri et al.
10,668,227 B2 6/2020 Caspers
10,675,055 B2 6/2020 Chong et al.
10,675,333 B2 6/2020 Ning et al.
10,675,404 B2 6/2020 Pizzochero et al.
10,682,458 B2 6/2020 Wu et al.
10,682,460 B2 6/2020 Adams et al.
10,682,461 B2 6/2020 Oakes
10,682,463 B2 6/2020 Kamen et al.
10,685,749 B2 6/2020 Hayter et al.
10,688,241 B2 6/2020 Yang
10,688,243 B2 6/2020 Cabiri et al.
10,688,294 B2 6/2020 Cowan et al.
10,709,834 B2 7/2020 Chiu et al.
10,716,891 B2 7/2020 Saab et al.
10,716,893 B2 7/2020 Gray et al.
10,716,895 B2 7/2020 Brewer et al.
10,716,896 B2 7/2020 O'Connor et al.
10,716,926 B2 7/2020 Burton et al.
10,719,584 B2 7/2020 Drew
10,722,643 B2 7/2020 Gray et al.
10,722,646 B2 7/2020 Cole et al.
10,722,647 B2 7/2020 Gray et al.
10,722,650 B2 7/2020 Duke et al.
10,722,661 B2 7/2020 Mandro et al.
10,729,842 B2 8/2020 Hooven et al.
10,729,844 B2 8/2020 Cole et al.
10,737,015 B2 8/2020 Estes et al.
10,737,016 B2 8/2020 Smith et al.
10,737,021 B2 8/2020 Deck
10,737,024 B2 8/2020 Schmid
10,737,026 B2 8/2020 Teutsch
10,737,038 B2 8/2020 Cole et al.
10,744,257 B2 8/2020 Mandro et al.
10,751,467 B2 8/2020 Kamen et al.
10,751,468 B2 8/2020 Abal
10,751,476 B2 8/2020 Gazeley et al.
10,751,478 B2 8/2020 Nazzaro
10,757,219 B2 8/2020 Moskal
10,758,675 B2 9/2020 Mazlish et al.
10,758,683 B2 9/2020 Gibson et al.
10,758,721 B2 9/2020 Sonderegger et al.
10,765,801 B2 9/2020 McCullough et al.
10,765,803 B2 9/2020 Gonnelli et al.
10,765,807 B2 9/2020 Allis et al.
10,772,796 B2 9/2020 Kavazov
10,773,019 B2 9/2020 Searle et al.
10,780,215 B2 9/2020 Rosinko et al.
10,780,216 B2 9/2020 Farra
10,780,217 B2 9/2020 Nazzaro et al.
10,780,220 B2 9/2020 Gray
10,780,223 B2 9/2020 Desborough et al.
10,792,419 B2 10/2020 Kamen et al.
10,792,424 B2 10/2020 Sasaki
10,792,440 B2 10/2020 Mandro et al.
10,799,630 B2 10/2020 McCullough et al.
10,799,631 B2 10/2020 Barmaimon et al.
10,799,632 B2 10/2020 Kohlbrecher
10,806,851 B2 10/2020 Rosinko
10,806,854 B2 10/2020 O'Connor et al.
10,806,855 B2 10/2020 Destefano et al.
10,806,859 B2 10/2020 Desborough et al.
10,814,061 B2 10/2020 Bene et al.
11,357,912 B2* 6/2022 Schøndorff ....... A61M 25/0068
2002/0052576 A1* 5/2002 Massengale ...... A61M 25/0074 604/164.01
2002/0156430 A1* 10/2002 Haarala ............ A61M 25/0075 604/247
2003/0093029 A1 5/2003 McGuckin et al.
2003/0187394 A1 10/2003 Wilkinson et al.
2004/0054351 A1* 3/2004 Deniega ................ A61M 29/00 604/537
2004/0176743 A1* 9/2004 Morris ............. A61M 25/0075 604/537
2005/0065466 A1 3/2005 Vedrine
2005/0177131 A1* 8/2005 Lentz ................ A61M 25/0054 604/525
2005/0216047 A1* 9/2005 Kumoyama ...... A61M 25/1027 606/191
2005/0283122 A1* 12/2005 Nordgren .......... A61M 25/0075 604/247
2006/0106346 A1 5/2006 Sullivan et al.
2006/0149191 A1* 7/2006 DiFiore ............ A61M 25/0075 604/246
2007/0124002 A1 5/2007 Estes et al.
2007/0191770 A1 8/2007 Moberg et al.
2008/0215035 A1 9/2008 Yodfat et al.
2008/0234630 A1 9/2008 Iddan et al.
2008/0255447 A1 10/2008 Bourang et al.
2009/0043372 A1* 2/2009 Northrop ........ A61M 25/09016 623/1.15
2009/0312718 A1* 12/2009 Onuma ............ A61M 25/0075 604/246
2009/0326453 A1 12/2009 Adams et al.
2010/0049128 A1 2/2010 McKenzie et al.
2010/0094251 A1 4/2010 Estes et al.
2010/0135831 A1 6/2010 Jacobsen
2010/0145303 A1 6/2010 Yodfat et al.
2010/0168670 A1 7/2010 Srisathapat et al.
2010/0211140 A1* 8/2010 Barbut .................. A61M 15/08 607/105
2010/0241103 A1 9/2010 Kraft et al.
2011/0040247 A1 2/2011 Mandro et al.
2011/0112484 A1 5/2011 Carter et al.
2011/0112696 A1 5/2011 Yodfat et al.
2011/0118578 A1 5/2011 Timmerman
2011/0160652 A1 6/2011 Yodfat et al.
2011/0160666 A1 6/2011 Hanson et al.
2011/0313357 A1 12/2011 Skutnik et al.
2012/0059285 A1 3/2012 Soltani et al.
2012/0078170 A1 3/2012 Smith et al.
2012/0136300 A1 5/2012 Schoonmaker et al.
2012/0150123 A1 6/2012 Lawrence et al.
2012/0172668 A1 7/2012 Kerns et al.
2012/0209085 A1 8/2012 Degen et al.
2012/0238851 A1 9/2012 Kamen et al.
2013/0046239 A1 2/2013 Gonnelli et al.
2013/0046508 A1 2/2013 Sur et al.
2013/0053823 A1 2/2013 Fiering et al.
2013/0060233 A1 3/2013 O'Connor et al.
2013/0138075 A1 5/2013 Lambert
2013/0138077 A1* 5/2013 O'Day .............. A61M 25/0015 83/866
2013/0226138 A1 8/2013 Sia
2013/0237955 A1 9/2013 Neta et al.
2013/0267912 A1* 10/2013 Cox .................. A61M 25/0015 29/890.12
2014/0025002 A1 1/2014 Qi et al.
2014/0031793 A1 1/2014 Constantineau et al.
2014/0052096 A1 2/2014 Searle et al.
2014/0054883 A1 2/2014 Anigan et al.
2014/0127048 A1 5/2014 Dilanni et al.
2014/0128815 A1 5/2014 Cabiri et al.
2014/0276379 A1 9/2014 Uram et al.
2014/0276536 A1 9/2014 Estes
2014/0323961 A1 10/2014 Blomquist et al.
2014/0358112 A1 12/2014 Smith et al.
2015/0025503 A1 1/2015 Searle et al.
2015/0051583 A1* 2/2015 Horvath ............ A61M 25/0015 604/523
2015/0073384 A1 3/2015 Limaye
2015/0080799 A1 3/2015 Schneider et al.
2015/0080800 A1 3/2015 Cronenberg et al.
2015/0105720 A1 4/2015 Montalvo et al.
2015/0112269 A1 4/2015 Sumida et al.
2015/0209505 A1 7/2015 Hanson et al.
2015/0223977 A1 8/2015 Oberkircher et al.

(56) References Cited

U.S. PATENT DOCUMENTS

2015/0273201 A1 10/2015 Tallarida et al.
2015/0314117 A1 11/2015 Arami et al.
2016/0051750 A1 2/2016 Tsoukalis
2016/0074578 A1 3/2016 Xu et al.
2016/0082182 A1 3/2016 Gregory et al.
2016/0089056 A1 3/2016 Limaye et al.
2016/0089524 A1 3/2016 Anderson
2016/0144105 A1 5/2016 Hooven et al.
2016/0193407 A1 7/2016 Qin et al.
2016/0346469 A1 12/2016 Shubinsky et al.
2017/0080157 A1 3/2017 Cabiri et al.
2017/0100542 A1 4/2017 Norton et al.
2017/0232191 A1 8/2017 Smith et al.
2017/0258987 A1 9/2017 Caspers
2017/0290971 A1 10/2017 Hedmann et al.
2017/0296741 A1 10/2017 Gregory
2017/0296742 A1 10/2017 Stefanov et al.
2017/0340827 A1 11/2017 Nazzaro et al.
2017/0340841 A1 11/2017 Sasaki
2017/0351841 A1 12/2017 Moskal
2017/0351851 A1 12/2017 Wang et al.
2017/0368260 A1 12/2017 McCullough et al.
2018/0008768 A1 1/2018 Prescher et al.
2018/0028744 A1 2/2018 Kim
2018/0036476 A1 2/2018 McCullough et al.
2018/0071450 A1 3/2018 Ruhland
2018/0110420 A1 4/2018 Pekander
2018/0185573 A1 7/2018 Niklaus
2018/0193563 A1 7/2018 Krasnow et al.
2018/0200434 A1 7/2018 Mazlish et al.
2018/0200440 A1 7/2018 Mazlish et al.
2018/0221571 A1 8/2018 Carbone et al.
2018/0344926 A1 12/2018 Brandenburg et al.
2018/0361061 A1 12/2018 Andretta
2018/0372085 A1 12/2018 Velschow et al.
2019/0009022 A1 1/2019 Oakes
2019/0083057 A1 3/2019 Saul et al.
2019/0175828 A1 6/2019 List et al.
2019/0262535 A1 8/2019 Shubinsky et al.
2019/0275243 A1 9/2019 Deck et al.
2019/0275249 A1 9/2019 von Campenhausen
2019/0282751 A1 9/2019 Della Bidia
2019/0290845 A1 9/2019 List et al.
2019/0298485 A1 10/2019 Forsell
2019/0298912 A1 10/2019 Spencer et al.
2019/0298914 A1 10/2019 Kamen et al.
2019/0298918 A1 10/2019 Jallon
2019/0298921 A1 10/2019 Stafford
2019/0298925 A1 10/2019 Cowe et al.
2019/0307943 A1 10/2019 Franano et al.
2019/0307954 A1 10/2019 Klemm et al.
2019/0307955 A1 10/2019 Levesque et al.
2019/0307970 A1 10/2019 Kamen et al.
2019/0314572 A1 10/2019 Yang
2019/0321544 A1 10/2019 List et al.
2019/0321545 A1 10/2019 Saint et al.
2019/0321546 A1 10/2019 Michaud et al.
2019/0321552 A1 10/2019 DiPerna et al.
2019/0328963 A1 10/2019 Wolff et al.
2019/0336678 A1 11/2019 Rule
2019/0336681 A1 11/2019 Kamen et al.
2019/0343434 A1 11/2019 Varsavsky et al.
2019/0344009 A1 11/2019 Damiano et al.
2019/0344010 A1 11/2019 Pizzochero et al.
2019/0350501 A1 11/2019 Blomquist et al.
2019/0351134 A1 11/2019 Cook et al.
2019/0351135 A1 11/2019 Naftalovitz et al.
2019/0351143 A1 11/2019 Egloff et al.
2019/0351209 A1 11/2019 Butziger et al.
2019/0358393 A1 11/2019 Marbet
2019/0358395 A1 11/2019 Olson et al.
2019/0358437 A1 11/2019 Schwartz et al.
2019/0365985 A1 12/2019 Zidon et al.
2019/0366012 A1 12/2019 Gross et al.
2019/0368484 A1 12/2019 Chappel et al.
2019/0374706 A1 12/2019 Cabiri et al.
2019/0374709 A1 12/2019 Cole et al.
2019/0374714 A1 12/2019 Rioux et al.
2019/0374719 A1 12/2019 Cabiri et al.
2019/0374757 A1 12/2019 Verhoeven et al.
2019/0381241 A1 12/2019 Bryant et al.
2019/0388609 A1 12/2019 Lanigan et al.
2019/0388614 A1 12/2019 Gyrn et al.
2019/0388615 A1 12/2019 Sonderegger et al.
2020/0001005 A1 1/2020 Politis et al.
2020/0001006 A1 1/2020 Pizzochero et al.
2020/0001007 A1 1/2020 Miesel et al.
2020/0009317 A1 1/2020 Cronenberg et al.
2020/0009318 A1 1/2020 Kamen et al.
2020/0009319 A1 1/2020 Ludolph
2020/0009331 A1 1/2020 Kamen et al.
2020/0016328 A1 1/2020 Cane et al.
2020/0016329 A1 1/2020 Schabbach et al.
2020/0016333 A1 1/2020 Soares et al.
2020/0016335 A1 1/2020 DiPerna et al.
2020/0023121 A1 1/2020 Thomas et al.
2020/0023129 A1 1/2020 Day et al.
2020/0030528 A1 1/2020 Burke et al.
2020/0030531 A1 1/2020 Day et al.
2020/0030532 A1 1/2020 Day et al.
2020/0030533 A1 1/2020 Day et al.
2020/0030592 A1 1/2020 Cheche
2020/0038588 A1 2/2020 Varsavsky et al.
2020/0046904 A1 2/2020 Schader et al.
2020/0054822 A1 2/2020 Dewey
2020/0054825 A1 2/2020 Kamen et al.
2020/0054826 A1 2/2020 Diianni et al.
2020/0054832 A1 2/2020 Jeong et al.
2020/0061287 A1 2/2020 Chappel et al.
2020/0069865 A1 3/2020 Day et al.
2020/0069869 A1 3/2020 Grant et al.
2020/0077340 A1 3/2020 Kruse
2020/0077948 A1 3/2020 Schmid
2020/0078511 A1 3/2020 Focht et al.
2020/0078513 A1 3/2020 Wei
2020/0086042 A1 3/2020 Kamen et al.
2020/0086043 A1 3/2020 Saint
2020/0101218 A1 4/2020 Shapley et al.
2020/0101226 A1 4/2020 Rosinko et al.
2020/0108204 A1 4/2020 Mazlish et al.
2020/0114069 A1 4/2020 Searle et al.
2020/0118676 A1 4/2020 Spohn et al.
2020/0121854 A1 4/2020 Norton et al.
2020/0121937 A1 4/2020 Yoder et al.
2020/0129692 A1 4/2020 Kim et al.
2020/0138852 A1 5/2020 Chattaraj et al.
2020/0138911 A1 5/2020 Joseph et al.
2020/0147304 A1 5/2020 Crouther et al.
2020/0147305 A1 5/2020 Estes
2020/0147309 A1 5/2020 Quinn et al.
2020/0164159 A1 5/2020 Chattaraj et al.
2020/0168316 A1 5/2020 Kamen et al.
2020/0171236 A1 6/2020 McCullough et al.
2020/0179592 A1 6/2020 Adams et al.
2020/0179594 A1 6/2020 Yodfat et al.
2020/0179602 A1 6/2020 Mazlish et al.
2020/0179603 A1 6/2020 Rosinko
2020/0188508 A1 6/2020 Estes
2020/0188580 A1 6/2020 Gregory et al.
2020/0188581 A1 6/2020 Diianni et al.
2020/0197600 A1 6/2020 Chow et al.
2020/0197621 A1 6/2020 Quinn et al.
2020/0206418 A1 7/2020 Gonnelli et al.
2020/0215264 A1 7/2020 Searle et al.
2020/0215273 A1 7/2020 Gibson et al.
2020/0222624 A1 7/2020 Destafano et al.
2020/0222625 A1 7/2020 Cabiri et al.
2020/0230314 A1 7/2020 Kondo et al.
2020/0246541 A1 8/2020 Neftel et al.
2020/0253632 A1 8/2020 Chong et al.
2020/0254174 A1 8/2020 Kruse et al.
2020/0261002 A1 8/2020 Pace
2020/0261643 A1 8/2020 Boyaval et al.
2020/0261645 A1 8/2020 Kamen et al.

(56) References Cited

U.S. PATENT DOCUMENTS

| | | | |
|---|---|---|---|
| 2020/0268962 | A1 | 8/2020 | Gamelin |
| 2020/0268975 | A1 | 8/2020 | Kim et al. |
| 2020/0269020 | A1 * | 8/2020 | Palmaz ................. A61M 25/10 |
| 2020/0272310 | A1 | 8/2020 | Vik et al. |
| 2020/0276386 | A1 | 9/2020 | Kamen et al. |
| 2020/0289743 | A1 | 9/2020 | Chiu et al. |
| 2020/0306446 | A1 | 10/2020 | Kamen et al. |
| 2020/0306448 | A1 | 10/2020 | Schmid |
| 2020/0316291 | A1 | 10/2020 | Gibson et al. |
| 2020/0321094 | A1 | 10/2020 | Saint et al. |
| 2020/0324048 | A1 | 10/2020 | O'Connor et al. |
| 2020/0324101 | A1 | 10/2020 | Hartmann et al. |
| 2020/0330679 | A1 | 10/2020 | Cronenberg et al. |
| 2020/0330680 | A1 | 10/2020 | Deck |
| 2020/0330701 | A1 | 10/2020 | Cole et al. |
| 2020/0335194 | A1 | 10/2020 | Jacobson et al. |
| 2020/0338257 | A1 | 10/2020 | Hooven et al. |
| 2020/0338262 | A1 | 10/2020 | Kamen et al. |
| 2020/0338264 | A1 | 10/2020 | Allis et al. |
| 2020/0338266 | A1 | 10/2020 | Estes |

FOREIGN PATENT DOCUMENTS

| | | | |
|---|---|---|---|
| WO | 2010084268 | A1 | 7/2010 |
| WO | 2013103864 | A1 | 7/2013 |
| WO | 2015094945 | A1 | 6/2015 |
| WO | 2018129519 | A1 | 7/2018 |

OTHER PUBLICATIONS

Extended European Search Report; European Patent Office; Application No. 26167713.2; Dated Jun. 10, 2026; 12 pages.

* cited by examiner

CANNULA AND INFUSION DEVICES

CROSS-REFERENCE TO RELATED APPLICATION

This application is a Continuation of U.S. application Ser. No. 16/071,428, filed Jul. 19, 2018, which is a National Stage Entry of PCT Application No. PCT/IB2017/000081, filed Jan. 19, 2017, which claims priority to U.S. Provisional Application No. 62/280,345 filed on Jan. 19, 2016, the content of each of which is incorporated herein in its entirety.

FIELD OF THE DISCLOSURE

This disclosure describes infusion and cannula devices and methods for use of the infusion and cannula devices. The medical devices disclosed herein are configured for introduction of a therapeutic agent (e.g., a drug), including a therapeutic liquid or suspension or other suitable material, into a subject. In certain embodiments, the medical device is an infusion device comprising a cannula configured for this purpose.

BACKGROUND

Infusion devices comprising a flexible cannula, are designed to be inserted into the skin by means of an introducer needle and the needle is then removed. A therapeutic agent, such as insulin, is then delivered through the cannula. However, there is a risk that the cannula may become occluded (e.g., obstructed) upon delivery of the therapeutic agent. This can happen when the tip of the cannula is blocked for instance by inflammation in the tissue, or due to kinking of the cannula.

It is therefore desirable to minimize the risk of blocking of the cannula outlet, and/or the risk that kinking obstructs the discharge of the therapeutic agent (e.g., a drug). Previous attempts to circumvent these obstructions, including the use of cannulas with several openings (see, e.g., US Patent Pre-Grant Publication No. 2013/0245555) have been reported, but the risk of kinking and occlusion (e.g., obstruction) still remains.

SUMMARY

This disclosure describes methods and devices, that in some cases, can reduce or minimize the drawbacks and issues of cannula and infusion devices, including partial and/or complete occlusion and/or insufficient delivery of therapeutic agents to a subject in a simple, reliable and safe infusion device without substantially increasing the cost of the device.

In certain embodiments, disclosed herein are infusion devices comprising a cannula, the cannula having a tubular body member comprising a tubular wall. In some embodiments, the tubular wall of the cannula encloses a longitudinal extending internal bore. In other embodiments, the distal portion of the tubular wall comprises a distal end comprising at least one tip opening.

In some embodiments, provided herein is a cannula, wherein the cannula comprises at least two weakened portions in the tubular wall, a first weakened portion and a second weakened portion in the distal end of the tubular wall of the cannula and having a compression strength being (a/k/a compressive strength) smaller than the compression strength of the remaining part of the distal portion of the cannula, wherein the cannula is adapted to flex in an area comprising the weakened portions when for example the cannula is exposed to a compression force and/or an increased internal pressure taking place inside the longitudinal extending bore, wherein the fluid pressure at the weakened portion exceeds the fluid pressure at the tip opening, whereby at least one of the weakened portions provides a fluid communication between the internal bore and the outside of the cannula. In some embodiments, the increased internal pressure is caused by the flow of a therapeutic agent or other liquid, solution or suspension flowing through the distal portion of the cannula.

In yet other embodiments, the cannula disclosed herein comprises at least two weakened portions in the tubular wall: a first weakened portion and a second portion, the second weakened portion in the distal end of the cannula and having a compression strength smaller than the compression strength of the remaining part of the distal portion. In some embodiments, the cannula is adapted to flex in an area comprising the weakened portions when the cannula is exposed to a compression force and/or an increased fluid (e.g., flow of a therapeutic agent) pressure which may take place inside the longitudinal extending bore of the distal end of the cannula tip. In yet other embodiments, at least one of the weakened portions of the tubular wall provides a fluid communication between the internal bore and the outside of the cannula.

In some embodiments, provided herein are cannulas for subcutaneous infusion of a therapeutic agent, the cannula comprising a tubular body member comprising a tubular wall at least partly enclosing a longitudinal extending internal bore, the distal portion of the tubular body member having a distal tip end comprising at least one tip opening, wherein the tubular wall comprises at least two weakened portions in the wall, the weakened portions being capable of allowing the cannula to flex in an area comprising the weakened portions when the cannula is exposed to a compression force and/or an increased internal pressure.

In some embodiments, at least one of the weakened portions of the cannulas described herein is in the distal portion of the tubular body member. In another embodiment, the weakened portions comprise a slit, hole or groove. In some embodiments, the weakened portions result from the material properties of the tubular wall. In still other embodiments, the weakened portions result from a portion of the tubular wall being thinner as compared to the rest of the wall. In yet other embodiments, at least one of the weakened portions comprises a slit, hole or groove. In still other embodiments, the weakened portion in the distal portion of the tubular body member is a slit, hole or groove. In some instances, the weakened portion is a slit.

In some embodiments, the number of weakened portions of the cannulas described herein is less than 10. In other embodiments, the number of weakened portions is between 2-10, between 2-8, between 2-6 or between 2-4. In still other embodiments, the number of weakened portions is 2. In yet other embodiments, at least a portion of the therapeutic agent is released from the distal tip end. In still other embodiments, each of the weakened portions have a compression strength smaller than the compression strength of the remaining portions of the tubular body member. In some embodiments, when the cannula is exposed to a compression force and/or an increased internal pressure and the internal pressure in the longitudinal extending bore exceeds the internal pressure that the tip opening, at least one of the weakened portions provides a fluid communication between the internal bore and the outside of the cannula. In still other embodiments, the weakened portion providing the fluid communication is a slit, hole or groove in the distal portion of the tubular body member.

In select embodiments, each of the weakened portions of the cannulas described herein are at the same distance from the tip opening. In still other embodiments, the weakened portions have an extension in the longitudinal direction parallel with the longitudinal axis of the cannula, the length of the weakened portions being 0.2-1.5 mm, or 0.4-0.8 mm, or 0.4-0.6 mm. In other embodiments, a longitudinal axis of each weakened portion forms an angle with a longitudinal axis of the cannula, wherein the angle is not 90°. In some embodiments, a longitudinal axis of each weakened portion forms an angle with a longitudinal axis of the cannula, wherein the angle is substantially 0°. In some embodiments, each of the weakened portions are formed as a slit and located at the same circumferential location of the tubular body. In other embodiments, the weakened portions comprises 2-10 slits, or 2-8 slits and is formed at the same circumferential location of the tubular body. In still other embodiments, one of the weakened portions is a corrugated portion. In still other embodiments, each of the weakened portions are at least 0.25-2.5 mm, or 0.5-1.5 mm, or 0.75-1.25 mm from the tip opening and extends towards the proximal portion of the cannula.

In some embodiments, at least two of the weakened portions of the cannulas described herein are formed at the same circumferential location of the tubular body member, and the first weakened portion is approximately opposite the second weakened portion. In some embodiments, the weakened portions all are formed as slits and formed at the same circumferential location of the tubular body member wherein the slits extend in the longitudinal direction parallel with the longitudinal axis of the internal bore, the length of the slits being 0.2-1.5 mm, or 0.4-0.8 mm, or 0.4-0.6 mm. In other embodiments, the weakened portions all are formed as slits and formed at the same circumferential location of the tubular body member, the slits providing slats between the slits, the slats adapted to flex outwards away from the internal bore, when the cannula is exposed to compression forces or/and an increased internal pressure. In still other embodiments, the slats are delimited by sidewalls parallel to the longitudinal axes of the tubular body member and the sidewalls delimiting each slat are parallel to each other in a radial direction. In yet other embodiments, the slats are delimited by sidewalls parallel to the longitudinal axes of the tubular body member, the sidewalls for each slat converging in a radial direction towards the outside of the tubular body, whereby the openings provided by the slits are converging towards the internal bore. In some embodiments, each the weakened portions are formed as slits and formed at the same circumferential location of the tubular body member, the slits providing slats between the slits, wherein the slats are adapted to flex outwards away from the internal bore when the cannula is exposed to compression forces and/or the internal pressure exceeds the pressure at the tip opening. In another embodiment, the second weakened portion comprises a side opening having a circular or oval cross-sectional area permitting communication from the inside of the tubular body to the outside of the tubular body the first and second weakened portion are formed at the same circumferential location of the tubular body and substantially opposite each other. In still another embodiment, the first weakened portion comprises a part of the wall of the tubular body member being formed corrugated in the region and shaped into alternate ridges and grooves.

In some embodiments, the distal portion of the cannulas described herein is subcutaneously placed and comprises PTFE (polytetrafluoroethylene; Teflon), FEP (fluorinated ethylene propylene), rubber, PE (polyethylene) material or silicone base materials. In some embodiments, the cannula is insertable with an insertion needle. In yet other embodiments, each of the weakened portions are positioned below a basal membrane of the skin when the cannula is subcutaneously placed. In still other embodiments, a length of the distal end of the cannula is less than 3.5 mm, and an outer diameter of the distal end is less than 1.5 mm.

In some embodiments provided herein are infusion devices for subcutaneously delivery of a therapeutic agent to a patient comprising: a cannula comprising a tubular body member comprising a tubular wall at least partly enclosing a longitudinal extending internal bore, the distal portion of the tubular body member having a distal tip end comprising at least one tip opening, wherein the tubular wall comprises at least two weakened portions in the wall, the weakened portions being capable of allowing the cannula to flex in an area comprising the weakened portions when the cannula is exposed to a compression force and/or an increased internal pressure; and a hub part configured to be fastened onto the subject or patient's skin via a mounting pad.

In some embodiments, at least one of the weakened portions of the infusion devices disclosed herein is in the distal portion of the tubular body member. In another embodiment, the weakened portions comprise a slit, hole or groove. In yet other embodiments, the weakened portions result from the material properties of the tubular wall. In still other embodiments, the weakened portions result from a portion of the tubular wall being thinner as compared to the rest of the wall. In some embodiments, at least one of the weakened portions comprises a slit, hole or groove. In some embodiments, the weakened portion in the distal portion of the tubular body member is a slit, hole or groove. In some embodiments, the number of weakened portions is less than 10. In yet other embodiments, the number of weakened portions is between 2-10, between 2-8, between 2-6 or between 2-4. In still other embodiments, the number of weakened portions is 2.

In some embodiments, at least a portion of the therapeutic agent in the infusions devices disclosed herein is released from the distal tip end of the cannula. In some embodiments, each of the weakened portions have a compression strength smaller than the compression strength of the remaining portions of the tubular body member. In another embodiment, when the cannula is exposed to a compression force and/or an increased internal pressure and the internal pressure in the longitudinal extending bore exceeds the internal pressure that the tip opening, at least one of the weakened portions provides a fluid communication between the internal bore and the outside of the cannula. In still other embodiments, the weakened portion providing the fluid communication is a slit, hole or groove in the distal portion of the tubular body member. In an embodiment, each of the weakened portions are at the same distance from the tip opening. In still other embodiments, the weakened portions have an extension in the longitudinal direction parallel with the longitudinal axis of the cannula, the length of the weakened portions being 0.2-1.5 mm, or 0.4-0.8 mm, or 0.4-0.6 mm. In still other embodiments, a longitudinal axis of each weakened portion forms an angle with a longitudinal axis of the cannula, wherein the angle is not 90°. In other embodiments, a longitudinal axis of each weakened portion forms an angle with a longitudinal axis of the cannula, wherein the angle is substantially 0°. In yet other embodiments, each of the weakened portions are formed as a slit and located at the same circumferential location of the tubular body.

In some embodiments, the weakened portions of the infusion devices disclosed herein comprises 2-10 slits, or 2-8 slits and is formed at the same circumferential location of the tubular body. In some embodiments, one of the weakened portions is a corrugated portion. In some embodiments, each of the weakened portions are at least 0.25-2.5 mm, or 0.5-1.5 mm, or 0.75-1.25 mm from the tip opening and extends towards the proximal portion of the cannula. In yet other embodiments, at least two of the weakened portions are formed at the same circumferential location of the tubular body member, and the first weakened portions is approximately opposite the second weakened portion. In still other embodiments, the weakened portions all are formed as slits and formed at the same circumferential location of the tubular body member wherein the slits extend in the longitudinal direction parallel with the longitudinal axis of the internal bore, the length of the slits being 0.2-1.5 mm, or 0.4-0.8 mm, or 0.4-0.6 mm. In yet another embodiment, the weakened portions all are formed as slits and formed at the same circumferential location of the tubular body member, the slits providing slats between the slits, the slats adapted to flex outwards away from the internal bore, when the cannula is exposed for compression forces or/and an increased internal pressure. In still other embodiments, the slats are delimited by sidewalls parallel to the longitudinal axes of the tubular body member and the sidewalls delimiting each slat are parallel to each other in radial direction. In some embodiments, the slats are delimited by sidewalls parallel to the longitudinal axes of the tubular body member the sidewalls for each slat converging in radial direction towards the outside of the tubular body whereby the openings provided by the slits are converging towards the internal bore. In yet another embodiment, the slats are capable of bending approximately in the middle of the slats.

In an embodiment, each the weakened portions of the infusion devices disclosed herein are formed as slits and formed at the same circumferential location of the tubular body member the slits provide slats between the slits, the slats are adapted to flex outwards away from the internal bore when the cannula is exposed for compression forces or the internal pressure exceeds the pressure at the tip opening. In some embodiments, the second weakened portion comprises a side opening having a circular or oval cross-sectional area permitting communication from the inside of the tubular body to the outside of the tubular body the first and second weakened portion are formed at the same circumferential location of the tubular body and substantially opposite each other. In another embodiment, the first weakened portion comprises a part of the wall of the tubular body member being formed corrugated in the region and shaped into alternate ridges and grooves. In still another embodiment, the distal portion of the cannula is subcutaneously placed and comprises PTFE (polytetrafluoroethylene; Teflon), FEP (fluorinated ethylene propylene), rubber, PE (polyethylene) material or silicone base materials. In still another embodiment, the cannula is insertable with an insertion needle.

In some embodiments, each of the weakened portions of the infusion devices disclosed herein are positioned below a basal membrane of the skin when the cannula is subcutaneously placed. In some embodiments, a length of the distal end of the cannula is less than 3.5 mm, and an outer diameter of the distal end is less than 1.5 mm. In other embodiments, the width of the slits is 10-200 μm, 10-100 μm or 10-50 μm.

In still other embodiments, each of the weakened portions are slits and offset in an axial direction with respect to one another, wherein the longitudinal axis of each of the slits are parallel to a longitudinal axis of the cannula. In yet other embodiments, each of the weakened portions are slits and each slit comprises an upper or proximal boundary closest to the proximal portion of the cannula, and a lower or distal boundary closest to the tip opening, wherein the upper boundaries are at the same distance from the tip opening of the cannula, and a longitudinal axis of each of the slits are each parallel to a longitudinal axis of the cannula. In some embodiments, the device further comprises a pump in fluid connection with a reservoir configured to store medication/drug. In yet another embodiment, the subcutaneously placed distal portion of the cannula comprises a soft material such as PTFE (polytetrafluoroethylene; Teflon), FEP (fluorinated ethylene propylene), rubber, PE (polyethylene) material or silicone base materials. In still other embodiments, the infusion device is configured for subcutaneous infusion of one or more therapeutic agents. In yet another embodiment, at least one of the therapeutic agents comprise insulin.

In another aspect, a cannula for subcutaneous infusion of a therapeutic agent includes a tubular body member comprising a tubular wall at least partly enclosing a longitudinal extending internal bore. A distal portion of the tubular body member is tapered and has a distal tip end having at least one tip opening. The tubular wall has six slits about a circumference of the tubular body, each of the slits extending across a boundary between a cylindrical shaped portion of the tubular body and a tapered distal portion. Each of the slits has a width in a range of 20-45 μm. The cannula is operable to flex in weakened areas comprising the slits when the cannula is exposed to at least one of a compression force or an increased internal pressure so as to allow therapeutic agent to flow out of the cannula through one or more of the slits.

Some implementations include one or more of the following features. For example, in some cases, three of the slits have a width in a range of 20-25 μm, and three of the slits have a width in a range of 40-45 μm. In some cases, each slit is equidistant from adjacent ones of the slits in a direction around the circumference of the tubular body. In some instances, a width of each of three particular ones of the slits is about twice as large as a width of a corresponding slit located about 180° from the particular slit.

Also disclosed herein are methods of administering a therapeutic agent via an infusion device, the method comprising providing a cannula comprising a tubular body member comprising a tubular wall at least partly enclosing a longitudinal extending internal bore, the distal portion of the tubular body member having a distal tip end comprising at least one tip opening, wherein the tubular wall comprises at least two weakened portions in the wall, the weakened portions being capable of allowing the cannula to flex in an area comprising the weakened portions when the cannula is exposed to a compression force and/or an increased internal pressure, wherein when: 1) the cannula is exposed to a compression force whereby the tip opening is substantially closed; or 2) the cannula is exposed to an increased internal pressure exceeding the pressure at the tip opening, wherein the compression force or increased internal pressure opens at least one of the weakened portions allowing fluid communication between the internal bore and the external environment, thereby discharging the therapeutic agent.

Other aspects, features and advantages will be readily apparent from the following detailed description, the accompanying drawings, and the claims.

DETAILED DESCRIPTION

Figure 1:
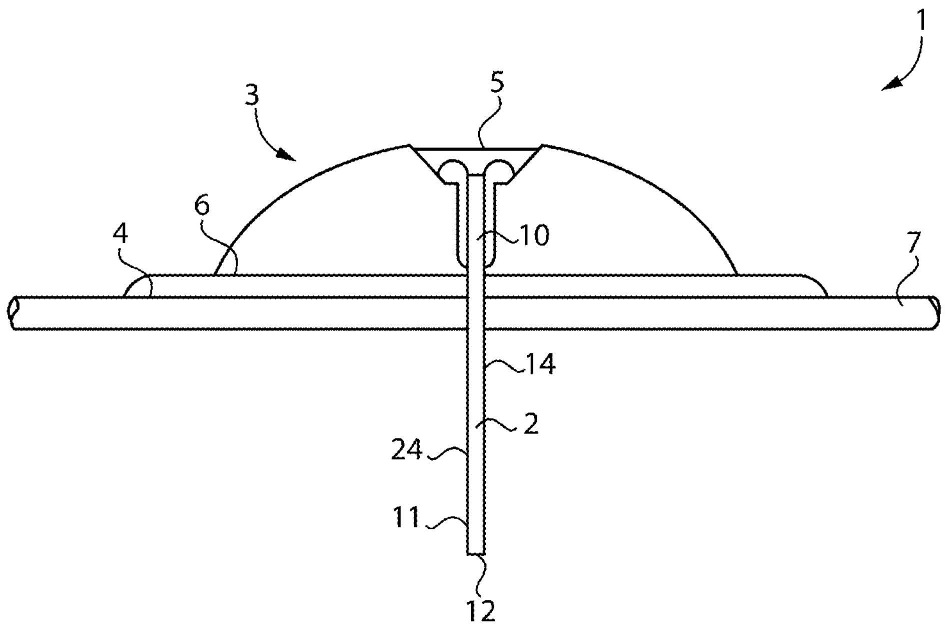
FIG. 1 shows an infusion device according to an embodiment disclosed herein.

Examples of the invention are now described with reference to the accompanying drawings.

This disclosure describes infusion devices that, in some cases, include: a cannula having a tubular body member with a proximal portion and a distal portion subcutaneously placed when the infusion device is placed on an outside surface of a patients skin, the tubular body member comprising a tubular wall enclosing a longitudinal extending internal bore, the distal portion having a distal end with a tip end comprising at least one tip opening, allowing a portion of a therapeutic agent (e.g., a drug) conveyed through the internal bore in the tubular body member to discharge; and a hub part configured to be fastened onto the patient's skin via a mounting pad.

This disclosure also describes cannulas that, in some cases, reduce or minimize kinking and/or occlusion of the subcutaneously placed devices. In some embodiments, the cannula comprises at least two weakened portions in the wall. In other embodiments, a first weakened portion and a second weakened portion is in the distal end of the wall of the cannula, wherein the weakened portions have a compression strength being smaller than the compression strength of the remaining part of the distal portion the cannula, wherein the cannula is adapted to flex in an area comprising the weakened portions when the cannula is exposed to a compression force and/or an increased therapeutic agent or internal pressure taking place inside the longitudinal extending bore, wherein the therapeutic agent or internal pressure exceeds the pressure at the tip opening, whereby at least one of the weakened portions provides a fluid communication between the internal bore and the outside of the cannula.

The expression "an area comprising the weakened portion" denotes that part of the cannula wall comprising the weakened portion or/and the neighboring wall of a weakened portion in circumferential direction of the cannula. Disclosed herein are cannulas comprising at least two weakened portions in the cannula wall. In some embodiments, the cannulas and devices disclosed herein comprises at least three weakened portions, at least four weakened portions, at least five weakened portions, at least six weakened portions, at least seven weakened portions, at least eight weakened portions, at least nine weakened portions or at least ten weakened portions in the cannula wall.

A "weakened portion" includes a part of the wall that has a smaller compression strength and/or requires a smaller force for elongation than the rest of the cannula wall, and may comprise, for example, a slit, a hole or a groove, or an area being thinner, e.g., wherein the weakened portion of the wall is between 0.1 μm to 0.5 mm thinner than the surrounding wall. The weakened portion may also be the result of specific materials at the site of the weakened portion, and thus has a smaller compression and elongation force than the rest of the cannula. In some embodiments, the materials in the weakened portion may comprise PTFE (polytetrafluoroethylene), rubber or PE (polyethylene).

FIG. 1 illustrates schematically an example of an infusion device 1. The infusion device 1 includes a cannula 2 having a tubular body member 14 with a proximal portion 10 and a subcutaneously placed distal portion 24 having a distal end 11. The distal portion 24 of the cannula 2 is provided with a tip opening 12 allowing a portion of a drug conveyed through the tubular body member 14 to discharge.

The infusion device according to FIG. 1 further includes a hub part 3 configured to be fastened onto an outside of the surface of a patients skin 7 via a mounting pad 4. The mounting pad 4 may be provided with an adhesive layer, configured to adhere to a patient's skin, and a not shown removable release liner that covers the adhesive layer. The mounting pad 4 may be a dressing, a plaster, an adhesive pad or the like, and the mounting pad may be configured in various shapes such as oval, circular, triangular rectangular etc. According to some implementations, the infusion device 1 may include the hub part 3 having a main plane being essentially parallel to the skin of the patient, when the infusion set is attached to a patient. The hub part 3 may have a main surface 6 being closest to the skin of a patient, and the main surface 6 may be provided with fastening means such as the mounting pad 4 for fastening the infusion device to the skin 7 of the patient.

In the embodiment according to FIG. 1, the cannula 2 extends from the hub part 3 through the fastening means or mounting pad 4. Alternatively, the cannula 2 may extend from the hub part 3 of the infusion device essentially along an inclined axis of insertion (not shown). As shown in FIG. 1, the hub part 3 may include a septum or barrier 5.

Figure 2A:
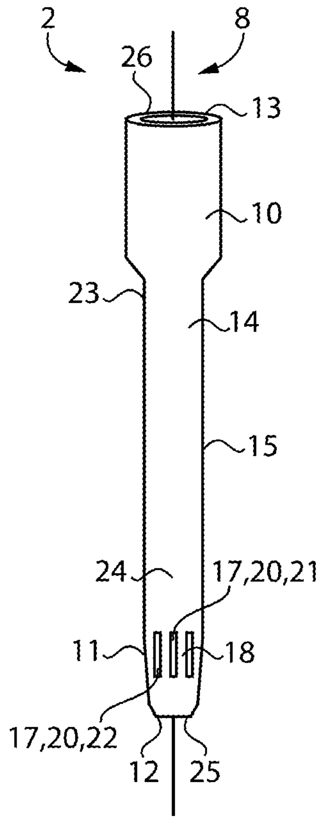
FIG. 2A is a planar view of an embodiment of the cannula disclosed herein.

As seen in FIG. 2A the cannula 2 is provided with a tubular body member 14 having a longitudinal extending internal bore 13—a conduit—extending along the longitudinal axis 8 of the cannula 2. A tubular wall 23 is surrounding the bore 13. (The conduit interconnects the infusion device with an inlet opening 26 in the top and a tip opening 12). The cannula 2 includes a proximal portion 10—configured for interconnection with the not shown infusion device—as well as a distal portion 24 configured for subcutaneously placement by means of an insertion needle (not shown).

Feature 12 refers to an outlet—the tip opening 12—arranged at the cannula tip 25 i.e., in the distal end 11 of the distal portion 24 of the cannula 2, opposite the interconnection with the infusion device. The outlet 12 may or may not be considered the primary outlet for drugs. In addition to the outlet 12, the cannula 2 is provided with weakened portions at least a first 21 and a second weakened 22 portion. In this embodiment, there is a number of weakened portions 20, each formed as slits 17 in the distal end 11 of the cannula. The slits (2-10 slits) are in the wall of the cannula 2 close to the tip 25 of the cannula 2 and all with substantially the same distance from the tip 25 and substantially with the same distance between the slits 17. The length of the slits is, in some cases, in a range of 0.2-1.5 mm, 0.4-0.8 mm, or 0.4-0.6 mm, and the distance of the weakened portion most distal to the tip of the cannula is in a range of 0.2-2.5 mm, 0.5-1.5 mm, or 0.75-1.25 mm and extends towards the proximal portion 10 of the cannula 2. The slits 17 are cut through the wall 23 allowing a fluid communication from the internal bore 13 to the outside of the cannula 2. The width of the slits 17 is, in some cases, in a range of 10-200 μm, 10-100 μm, or 10-50 μm. A laser may cut the slits 17.

The slits 17 may provide slats 18 between the slits 17. The slats 18 are flexible, and bend outwards when the cannula 2 is subjected to a compression force or an increased internal pressure. The sidewall of the slats 18 can be formed in different ways. This is illustrated in FIG. 3A and FIG. 3B which are cross-sections of the cannula in FIG. 2B along the line III-III. FIGS. 3A and 3B illustrates 2 embodiments of the slats 18. Additionally, in at least some of the figures, the width of the slits 17 is exaggerated for illustrative purposes. Further, while some of the figures show some of the slits 17 as narrow openings in the cannula 2, in some instances, each of the slits 17 is defined by a cut though the cannula 2 such that the slits 17 are normally in a closed or sealed configuration prior to flexing of the cannula and such that flexing of the cannula causes at least some of the slits 17 to open so as to allow the therapeutic agent to exit the cannula through the slits 17. In some instances, prior to flexing of the cannula, the slits 17 are closed or sealed such that the therapeutic agent does not exit through the slits.

The first embodiment shown in FIG. 3A shows a cannula 2 provided with six slits 17 thereby forming six slats 18 between them. The sidewalls 19 of the slats 18 are parallel to each other and parallel to the longitudinal axis 8 of the cannula 2 but all formed in such a way that the two side walls belonging to two opposing slats 18 form an opening/a slit 17 which is converging towards the internal bore 13. In some instances, the slits 17 are separated equidistantly from one another. In some instances, the distal end of the cannula 2 includes a tapered region where the tubular body member 14 forms the outlet 12. In some instances, the slits 17 are positioned on the cannula 2 across the intersection between the tapered region and a non-tapered region of the tubular body member 14. In some instances, the six slits 17 are 0.5 mm-0.8 mm in length along the tubular body member 14, and have a width of about 0.025 mm. The foregoing combination of features can be particularly advantageous ins some cases.

FIG. 3B shows a cannula 2 provided with six slits 17 and with six slats 18 between the slits 17. The sidewalls 19 of the slats 18 are parallel to each other and parallel to the longitudinal axis 8 of the cannula 2, but all formed in such a way, that the two side walls 19 belonging to two opposing slats 18 form a slit 17 that has parallel walls in the radial direction.

Figure 2B:
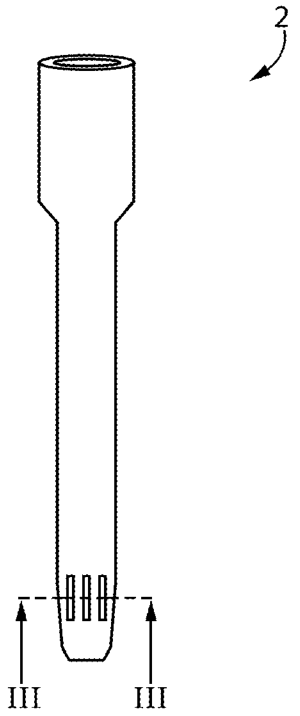
FIG. 2B is a planar view of an embodiment of the cannula disclosed herein.
Figure 3A:
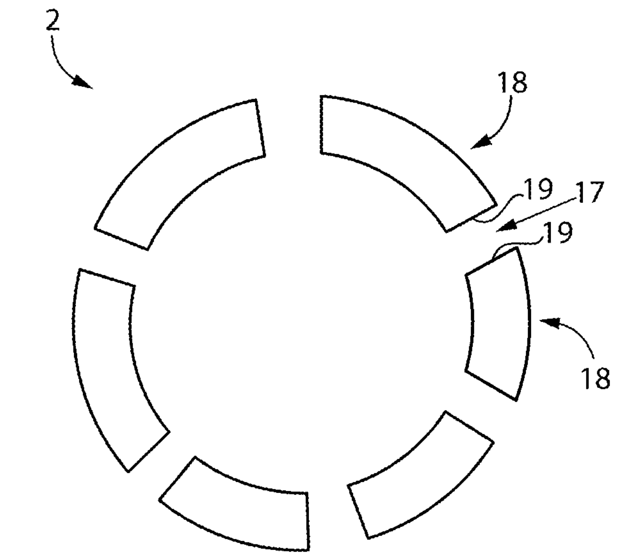
FIG. 3A is an embodiment of a cross-sectional view of the cannula shown in FIG. 2B.
Figure 3B:
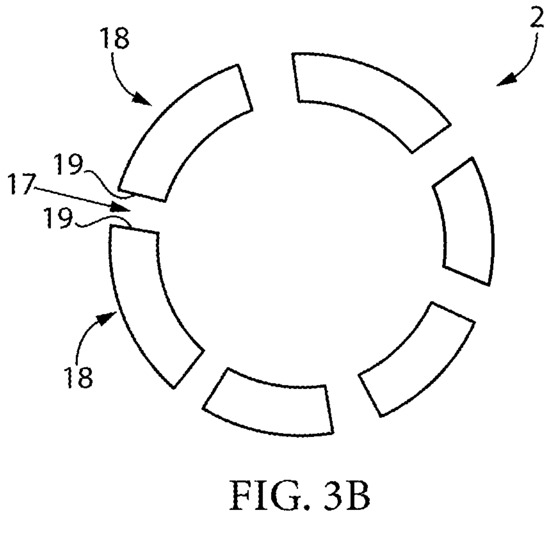
FIG. 3B is an alternative embodiment of a cross-sectional view of the cannula shown in FIG. 2B.
Figure 4:
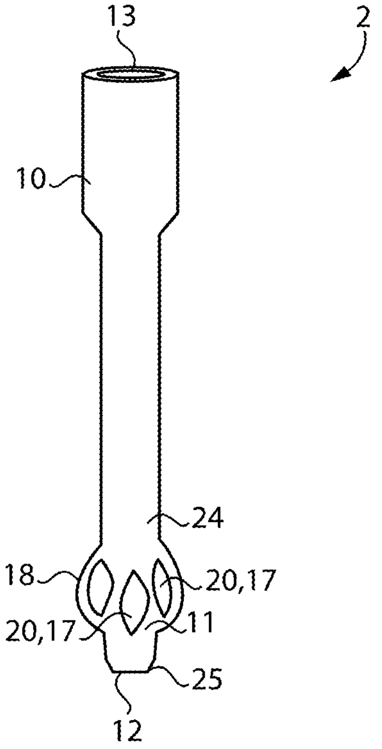
FIG. 4 shows a planar view of the embodiment shown in FIGS. 2A and 2B when exposed for a pressure.

FIG. 4 is a plane view of the embodiment shown in FIGS. 2A and 2B when exposed to a pressure. This pressure may arise from the tip 25 of the cannula 2 contacting a hard element. Instead of kinking, and thereby causing an obstruction, the weakened portions 20/slits 17 and the slats 18 provide a flexible portion of the distal end 11 of the cannula 2 in the area where the weakened portions 20/slits 17 and the slats 18 are positioned. The slats are bending outwards thereby providing several openings in the wall of the cannula allowing the drug to flow from the inside of the cannula 2 through the openings of the opened slits 17 and into the subcutaneous tissue. The pressure may also arise from internal pressure in the longitudinal extending internal bore 13. This may be caused by clogging of the tip opening 12 of the cannula 2 thereby preventing drug delivery through the tip opening 12. Due to the increased pressure, the slats 18 will bend outward away from the internal bore 13, and the slits 17 will open providing a fluid path from the inside of the cannula 2 to the subcutaneous tissue. When the pressure normalizes the openings/the slits 17 will close at least partly, and the drug will leave the cannula 2 through the tip opening 12 and optionally through the more or less closed slits 17.

Figure 5:
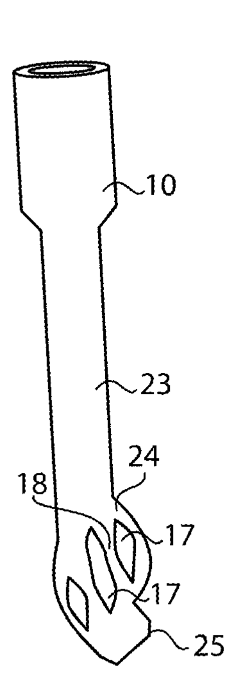
FIG. 5 shows a planar view of the embodiment shown in FIGS. 2A and 2B when exposed for a pressure having another attack of angle compared to the example shown in FIG. 4.

FIG. 5 is a plane view of the embodiment shown in FIGS. 2A and 2B when exposed to a pressure at an angle as compared to the example shown in FIG. 4. In this example it is illustrated that the slats 18 bend outwardly allowing the slits 17 to be opened, but the wall 23 of the cannula 2 is not exposed to the same compression force as in the case in FIG. 4. In FIG. 5 a small part of the tip contacts a hard element and thereby the compression force is only compressing the cannula on that side of the wall 23 where the element is located. Therefore, the slats 18 become most deformed in this area: that is they are bending outwards whereby the slits 17 are opened and provide openings on that side of the cannula 2 where the compression of the cannula 2 takes place.

Figure 6:
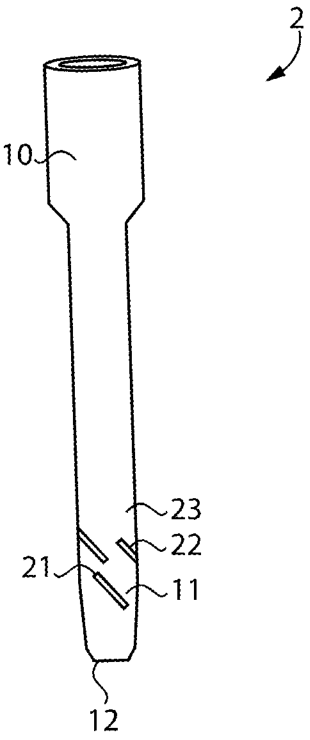
FIG. 6 shows a planar view of an alternative embodiment of a cannula applicable to the infusion devices disclosed herein.

FIG. 6 is a plane view of an embodiment of a cannula 2 applicable to the infusion device according to some implementations. In this embodiment, the weakened portions 21, 22 are formed as slits in the sidewall 23 of the cannula 2 and in the distal end 11. However, the first weakened portion 21 comprises several slits oblique in relation to the longitudinal axis of the internal bore. The second weakened 22 portion comprises fewer slits at the same circumferential level as the first weakened portion 21 but opposite the first weakened portion 21 and also obliquely positioned in relation to the longitudinal axis. In some instances, the second weakened portion 22 has only one slit. When an increased pressure takes place slits will open. When the cannula 2 is exposed to an increased compression force, the cannula will bend in the first weakened portion 21 as this is the portion having less compression strength. By the bending of the cannula, the slit(s) in the second weakened portion 22—opposite the first weakened portion 21 will open and thereby provide a fluid path.

Figure 7:
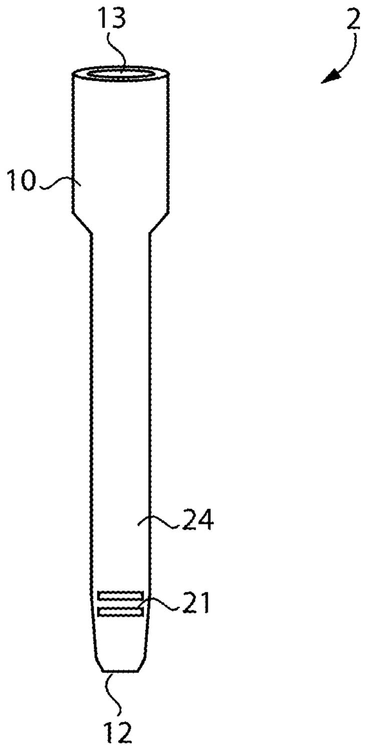
FIG. 7 shows a planar view of an alternative embodiment of a cannula applicable to the infusion devices disclosed herein.

FIG. 7 is a plane view of an embodiment of a cannula 2 applicable to the infusion device 1 according to some implementations. In this embodiment, the first weakened portion 21 comprises an area where the cannula 2 is formed with a wall thickness being smaller than the rest of the catheter wall. The first weakened portion 21 comprises several rectangular slits with their longitudinal axes perpendicular to the longitudinal axis of the internal bore. When the cannula 2 is exposed to pressure, the cannula 2 will bend in the area where the first weakened portion 21 is placed. Opposite the first weakened portion 21 a second weakened portion 22 is (not shown) being formed as an opening or a slit(s). Due to the bending of the cannula 2, the fluid will be pressed to flow out of the opening/slit(s).

Figure 8A:
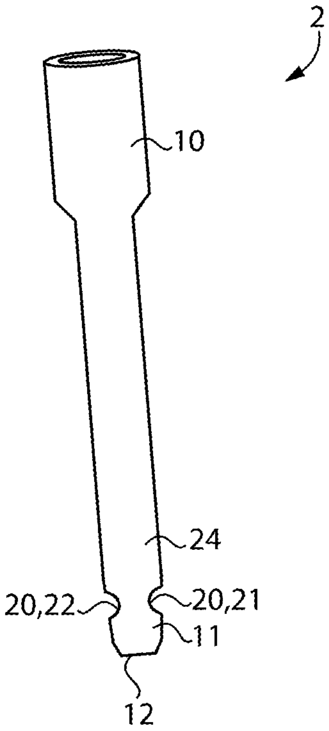
FIG. 8A shows a planar view of another embodiment of a cannula applicable to the infusion devices disclosed herein.
Figure 8B:
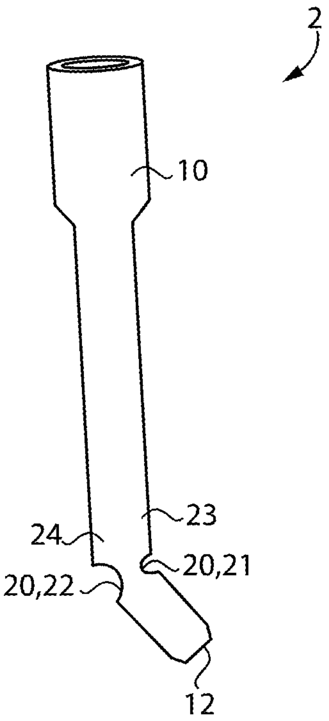
FIG. 8B shows a planar view of the embodiment shown in FIG. 8A when exposed to a pressure.

FIG. 8A is a plane view of an embodiment of a cannula 2 applicable to the infusion device 1 according to some implementations and FIG. 8B is a plane view of the embodiment shown in FIG. 8A when exposed to a pressure.

The embodiment works quite similar to the one shown in FIG. 7. The only difference is that the first weakened portion 21 is formed as a circular area in the distal end 11 of the cannula 2. The wall thickness of the first weakened portion 21 is smaller than the adjacent wall material of the cannula 2, or is made of another material, thereby providing a well-defined portion that will be deformed when exposed to an increased pressure.

This is shown in FIG. 8B where the cannula bends in the first weakened portion 21 to create an opening at the second weakened portion 22 thereby allowing the fluid through the opening 22 opposite the first weakened portion 21. When the cannula 2 is not exposed to kinking or occlusion of the outlet, the drug may then leave the bore through the tip and/or optionally through the opening provided by the second weakened portion 22.

Figure 9:
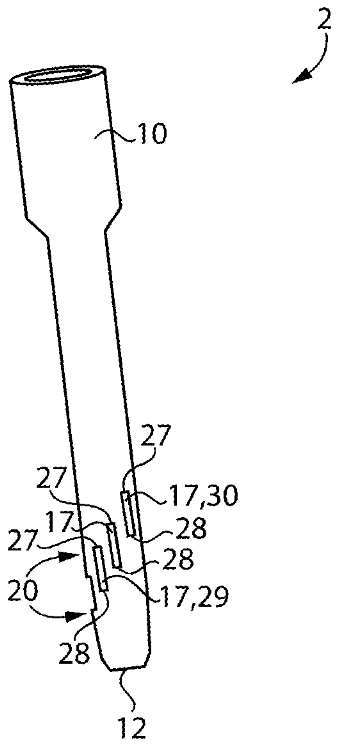
FIG. 9 shows a planar view of an alternative embodiment of a cannula applicable to the infusion devices disclosed herein.

FIG. 9 is a plane view of an embodiment of a cannula applicable to the infusion device according to some implementations. The difference between this embodiment and the one shown in FIG. 2 is that the weakened portions 20—all shaped as slits 17—are offset in axial direction with respect to one another. The longitudinal axes of the slits 17 are all parallel to the longitudinal axis of the cannula 2. Each slit 17 has an upper boundary/end 27 closest to the proximal portion 10 and an opposite lower boundary/end 28 closets to the tip opening 12. The upper boundary/end 27 of one slit 17 is in axial direction between an upper boundary/end 27 and a lower boundary/end 28 of a first neighboring slit 29. The lower boundary/end 28 of the same slit 17 is between an upper boundary/end 27 and a lower boundary/end 28 of a second neighboring slit 30.

The length of the distal end of the cannula 2 is, in some instances, less than 3.5 mm, e.g., in a range of 2.0-1.5 mm, and the outer diameter of the distal end 11 is less than 2 mm, and in some cases, less than 1.5 mm.

Figure 10A:
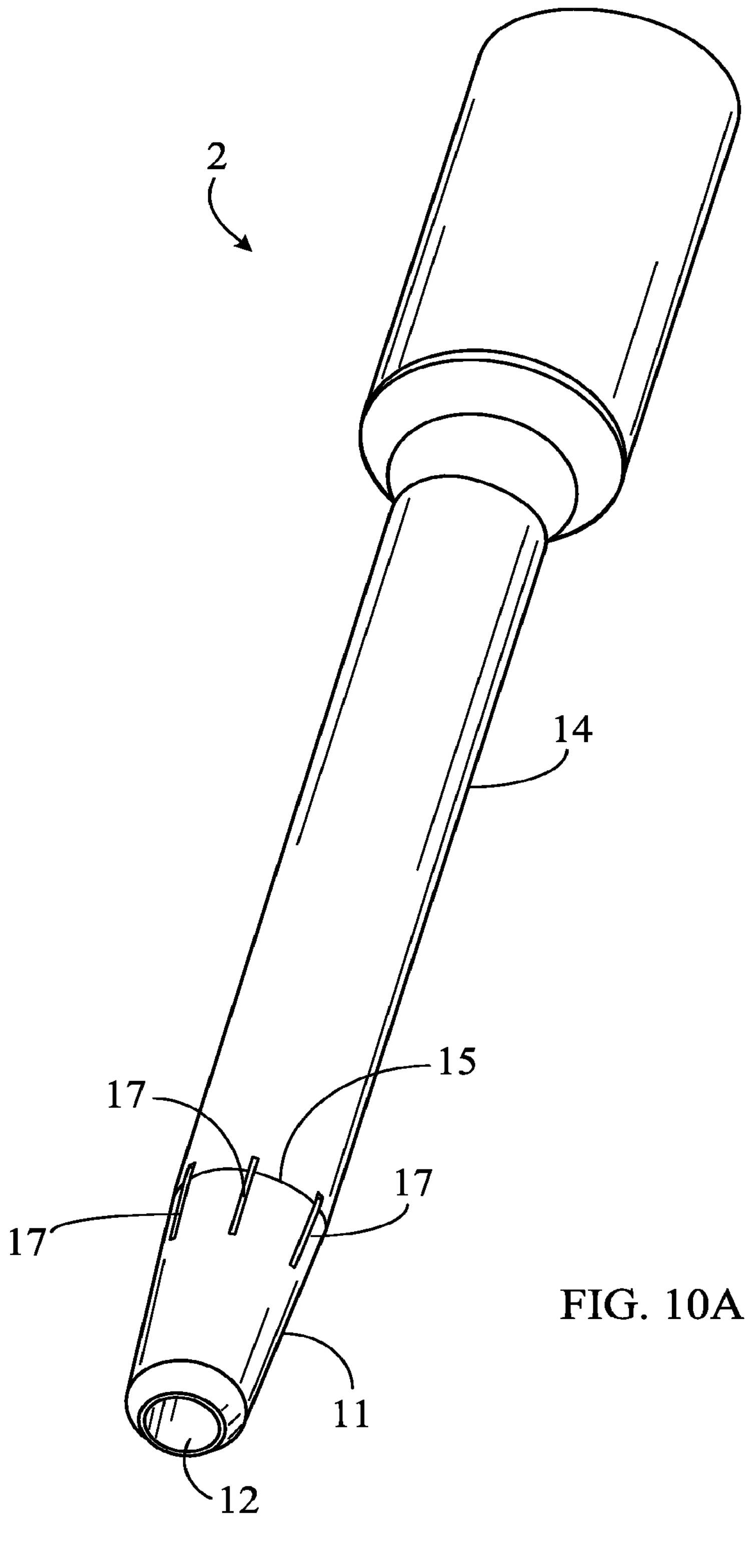
FIG. 10A shows an embodiment of a cannula applicable to the infusion devices disclosed herein.
Figure 10B:
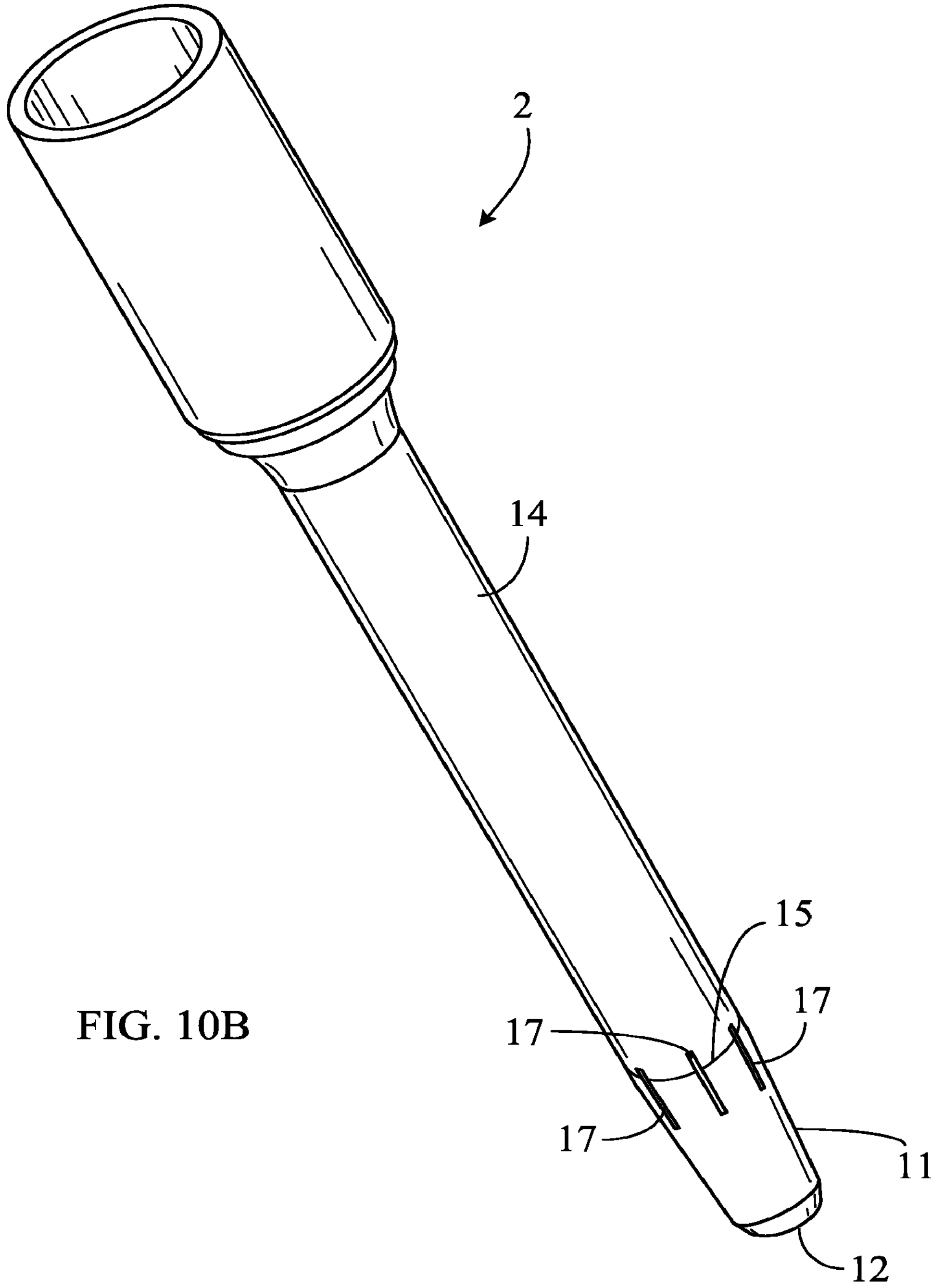
FIG. 10B shows an embodiment of a cannula applicable to the infusion devices disclosed herein.
Figure 10C:
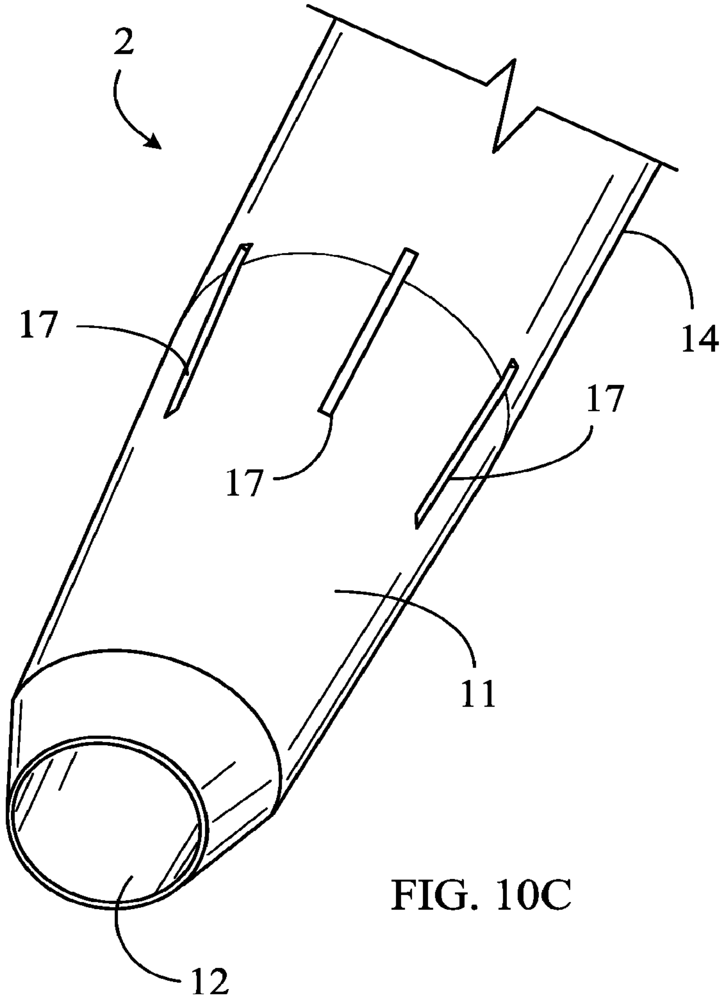
FIG. 10C shows an embodiment of a cannula applicable to the infusion devices disclosed herein.

FIGS. 10A, 10B and 10C illustrate an implementation in which the cannula 2 has six slits 17 in a direction of the length of the cannula tubular body member 14. FIG. 10A shows three of the six slits 17, and FIG. 10B shows the other three slits 17. In the illustrated example, each of the slits 17 is located at about the same distance from tip opening 12, and each slit 17 is substantially equidistant from adjacent slits 17 in a direction about the cannula circumference. Each of the slits 17 in the illustrated example extends across the transition, border or boundary 15 between the cannula tapered distal end 11 and the cannula cylindrical shaped body portion or tubular body member 14.

In some implementations, a laser beam is used to cut the narrow slits 17 through the cannula 2. In general, the width of the slits 17 may be based on the laser equipment used to form the slits. Further, in some instances, a single laser beam can form two slits substantially simultaneously, e.g., two slits that are separated by about 180° from one another. In some instances, the width of a slit 17 formed where the laser beam initially enters the side of the cannula 2 is in the range of about 20-25 μm, whereas the width of a slit 17 on the opposite side of the cannula 2 where the laser beam exits is in the range of about 40-45 μm. Thus, the width of the slits may differ from one another. In some cases, half of the slits 17 may have a first width, and the other half of the slits 17 may have a second width that differs from the first width. In some instances, the second width may be about twice as large as the first width. In some instances, the slits 17 are cut using a femtosecond laser. In some instances, the slits 17 are cut using a femtosecond laser where a first slit 17 and an opposing slit 17 are cut in the same instance. In some instances, the opposing slit 17 cut using a femtosecond laser is wider than the first slit 17. In some instances, the first slit 17 is 0.025 mm and the opposing slit 17 is 0.045 mm.

In some embodiments the distal portion and/or the distal end of the cannula 11, or in some cases the entire cannula 2, can be composed, for example, of a soft material such as PTFE (polytetrafluoroethylene; Teflon™), FEP (fluorinated ethylene propylene), rubber, PE material or silicone base materials and the like.

Figure 11A:
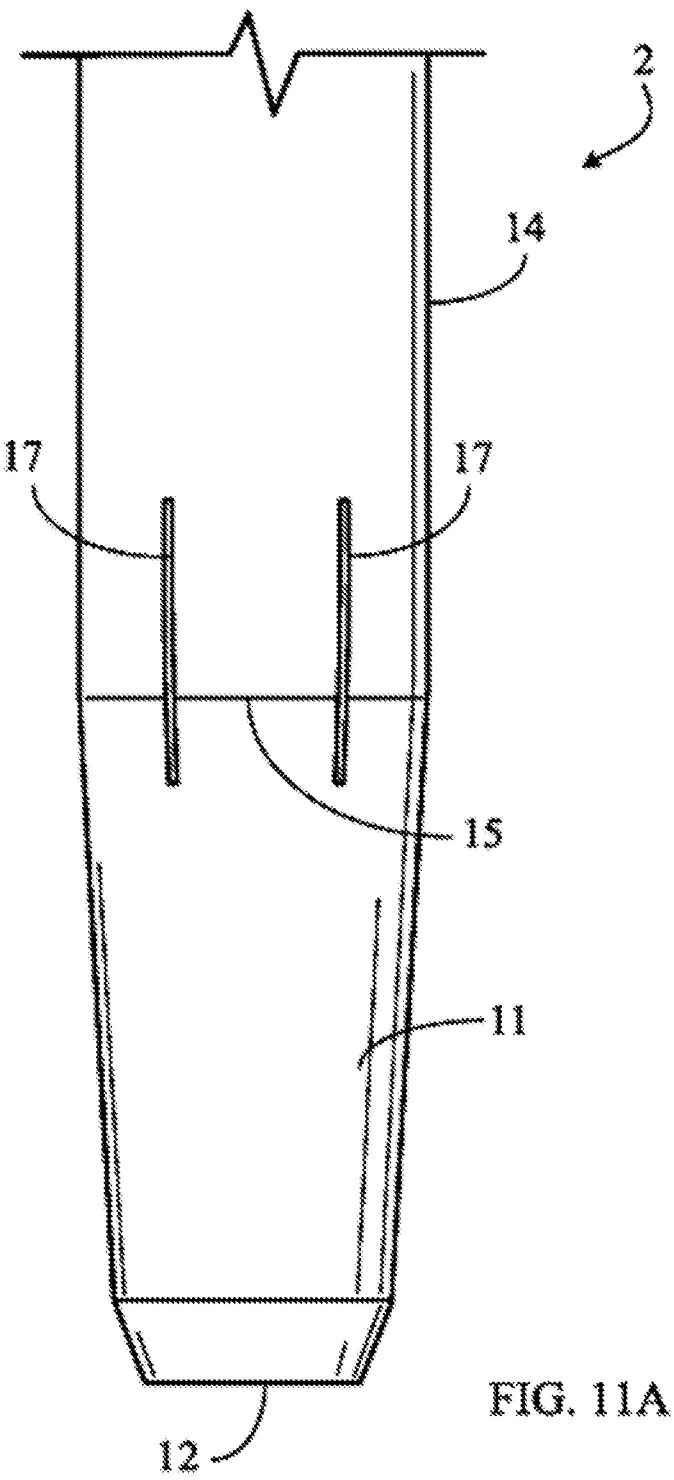
FIG. 11A shows deflection of the cannula embodiment of FIGS. 10A-10C.

As described above, soft cannulas can be impacted negatively by contact with tissue, which can cause bending or kinking of the cannula. Such bending or kinking can result in a decreased or interrupted flow of the therapeutic agent. FIG. 11A illustrates an example of the cannula of FIGS. 10A, 10B, 10C prior to impact (e.g., prior to the tip opening 12 contacting fascia or other tissue). When the cannula 2 is not exposed to kinking or occlusion of the tip opening 12, the therapeutic agent can leave the cannula bore through the tip opening 12 and/or through the slits 17.

Figure 11B:
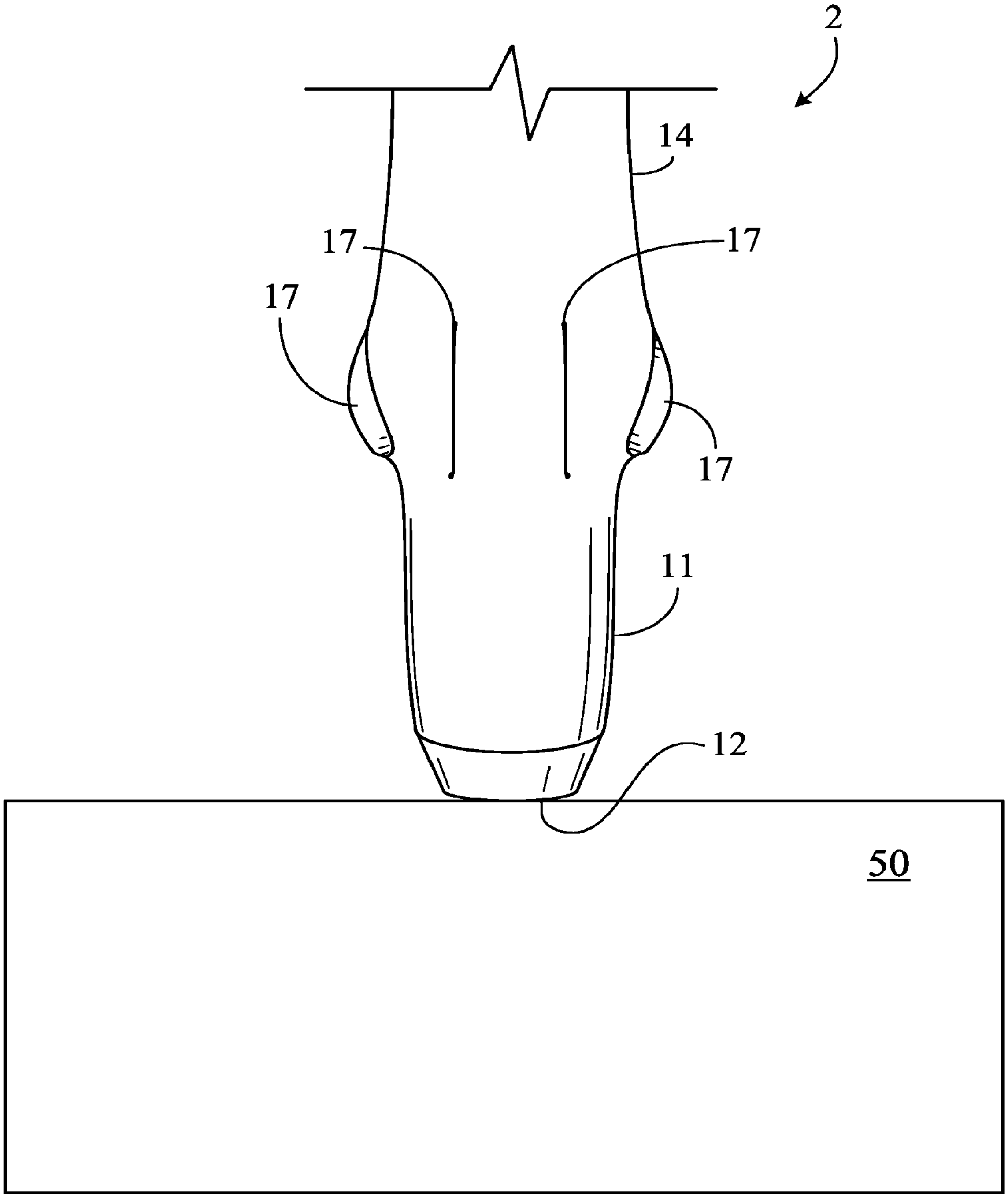
FIG. 11B shows deflection of the cannula embodiment of FIGS. 10A-10C.

On the other hand, the tip opening 12 may become obstructed or kinking may occur. FIG. 11B illustrates the tip opening 12 of the cannula 2 coming into straight or perpendicular contact with fascia or other tissue 50. The cannula 2 is adapted to flex in an area comprising the one or more slits 17 when the cannula is exposed to a significant compression force and/or an increased internal pressure inside the cannula longitudinal extending bore. Thus, if the tip opening 12 is obstructed, the pressure inside the cannula 2 increases and weakened portions comprising the slits 17 flex outward, thereby providing openings in the wall to allow the therapeutic agent to leave through the openings provided by the slits 17. Accordingly, even if the tip opening 12 is obstructed, one or more of the slits 17 can provide fluid communication between the internal bore and the outside of the cannula.

Figure 11C:
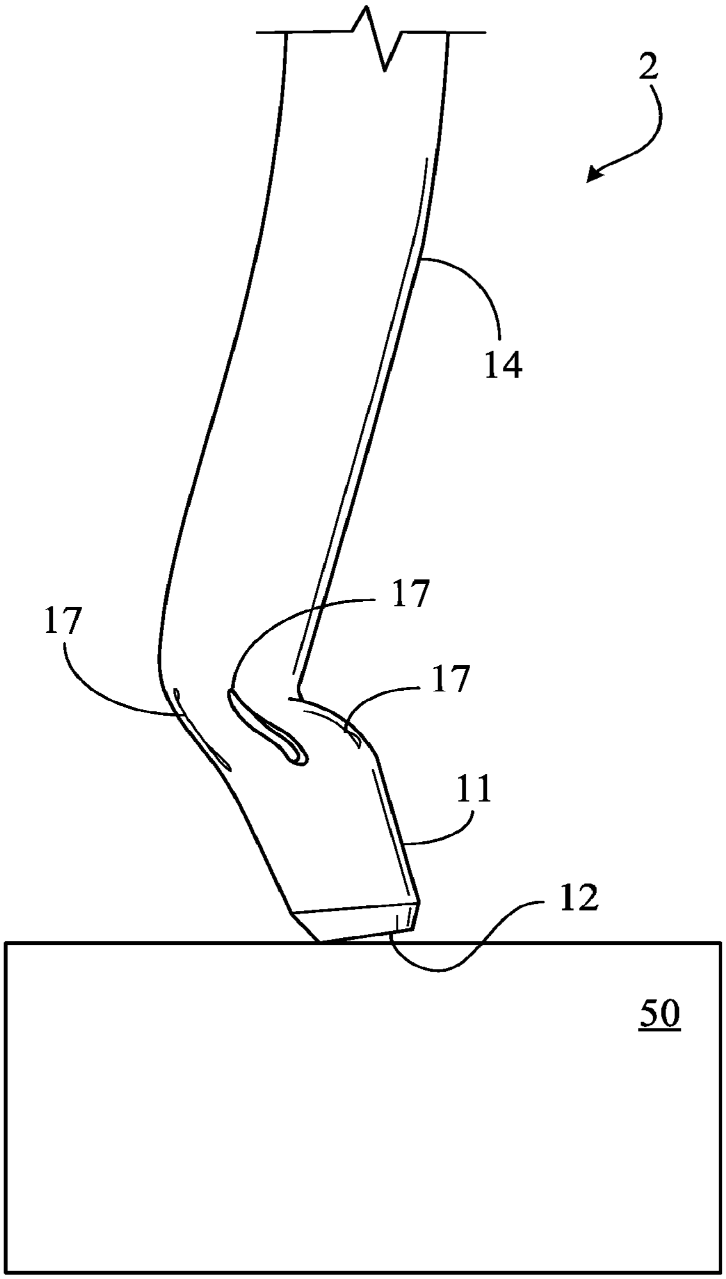
FIG. 11C shows deflection of the cannula embodiment of FIGS. 10A-10C.

Likewise, FIG. 11C illustrates the tip opening 12 of the cannula 2 coming into contact at an angle with fascia or other tissue 50. If kinking occurs in the cannula 2, the kinking will tend to occur at areas comprising one or more of the slits 17, thereby allowing the therapeutic agent to be delivered through one or more other slits 17 (e.g., slits on the opposite side of the cannula from where the kinking occurs).

Figure 12B:
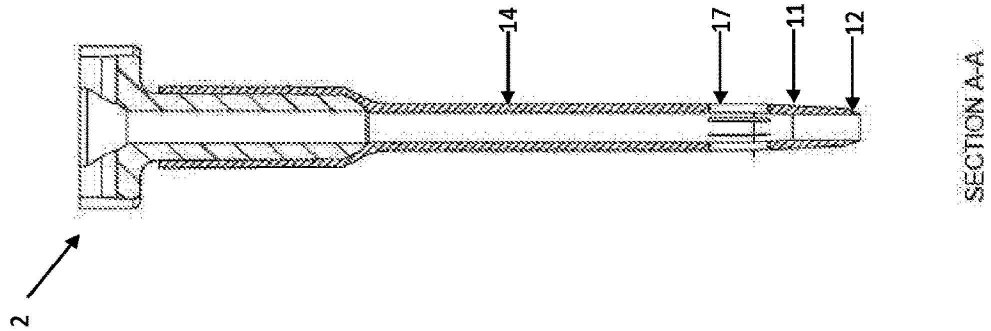
FIG. 12B shows an embodiment of a cannula applicable to the infusion devices disclosed herein.
Figure 12A:
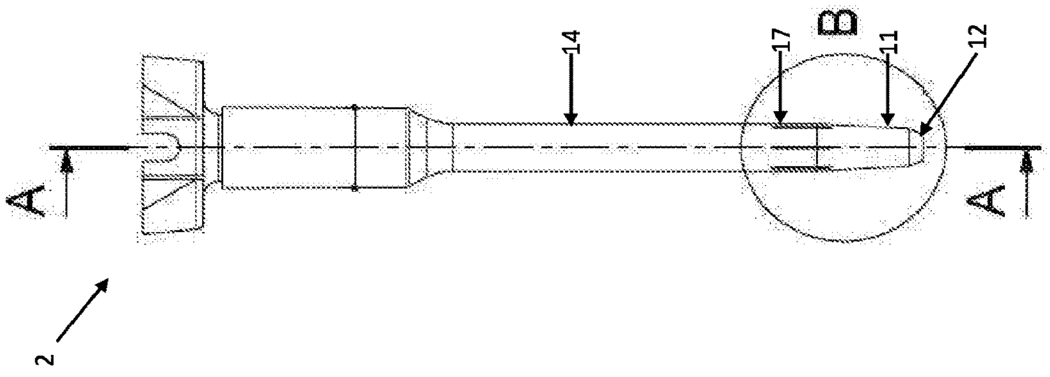
FIG. 12A shows an embodiment of a cannula applicable to the infusion devices disclosed herein.
Figure 12D:
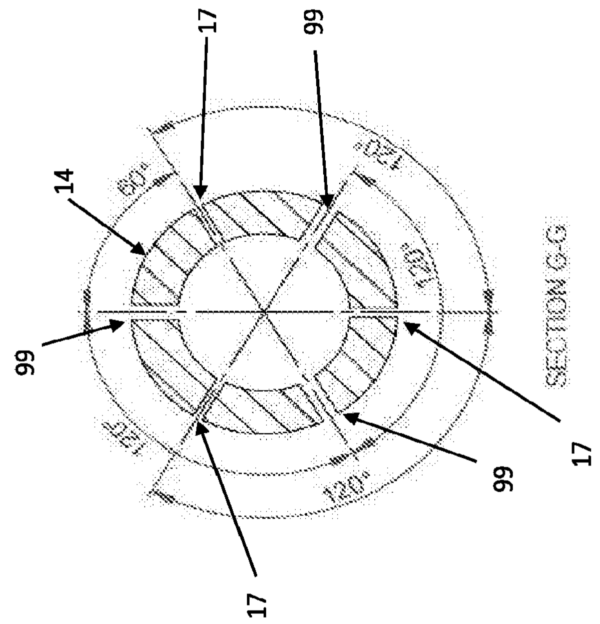
FIG. 12D shows an embodiment of a cannula applicable to the infusion devices disclosed herein.
Figure 12C:
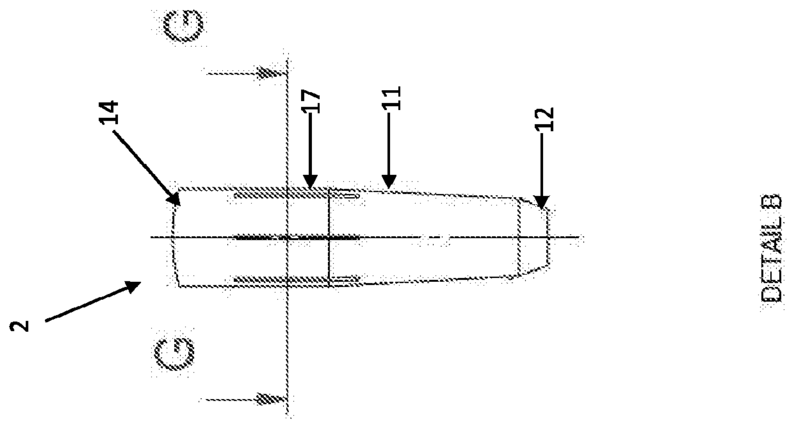
FIG. 12C shows an embodiment of a cannula applicable to the infusion devices disclosed herein.

FIGS. 12A-12D show an embodiment of a cannula applicable to the infusion devices disclosed herein. FIG. 12A illustrates a cannula 2 having a tubular body member 14 with six slits 17 at the distal portion of the cannula 2. FIG. 12B is a cross-section view of section A-A of FIG. 12A, and FIG. 12B shows the spacing of the six slits 17 at the border of the distal end 11 tubular body member 14 of the cannula 2. FIG. 12C is a detail view of detail B of FIG. 12A. FIG. 12C shows the location of the slits 17 at the border of the distal end 11 of the tubular body member 14. FIG. 12D is a radial cross-section view of the section G-G of FIG. 12C. FIG. 12D shows three slits 17 of a first size and opposing slits 99 of a larger size. FIG. 12D also illustrates an exemplary spacing pattern of the slits 17, 99 where, as illustrated, the slits 17, 99 are spaced equidistantly around the tubular body member 14. In some instances, the smaller slits 17 are approximately 0.025 mm wide, and the larger slits 99 are approximately 0.045 mm wide. In some instances, the slits 17, 99 are approximately 0.80 mm long and are disposed about 1.2 mm from the tip opening 12. In some instances, the distal end 11 is tapered and the border of the distal end 11 and the tubular body member 14 is about 1.4 mm from the tip opening 12. In some instances, and as shown in FIG. 12C, the distal end 11 includes a beveled edge or taper at the tip opening 12, and, in some instances, the beveled edge or taper is between 30° and 15° with respect to the longitudinal axis of the cannula 2.

Figure 13:
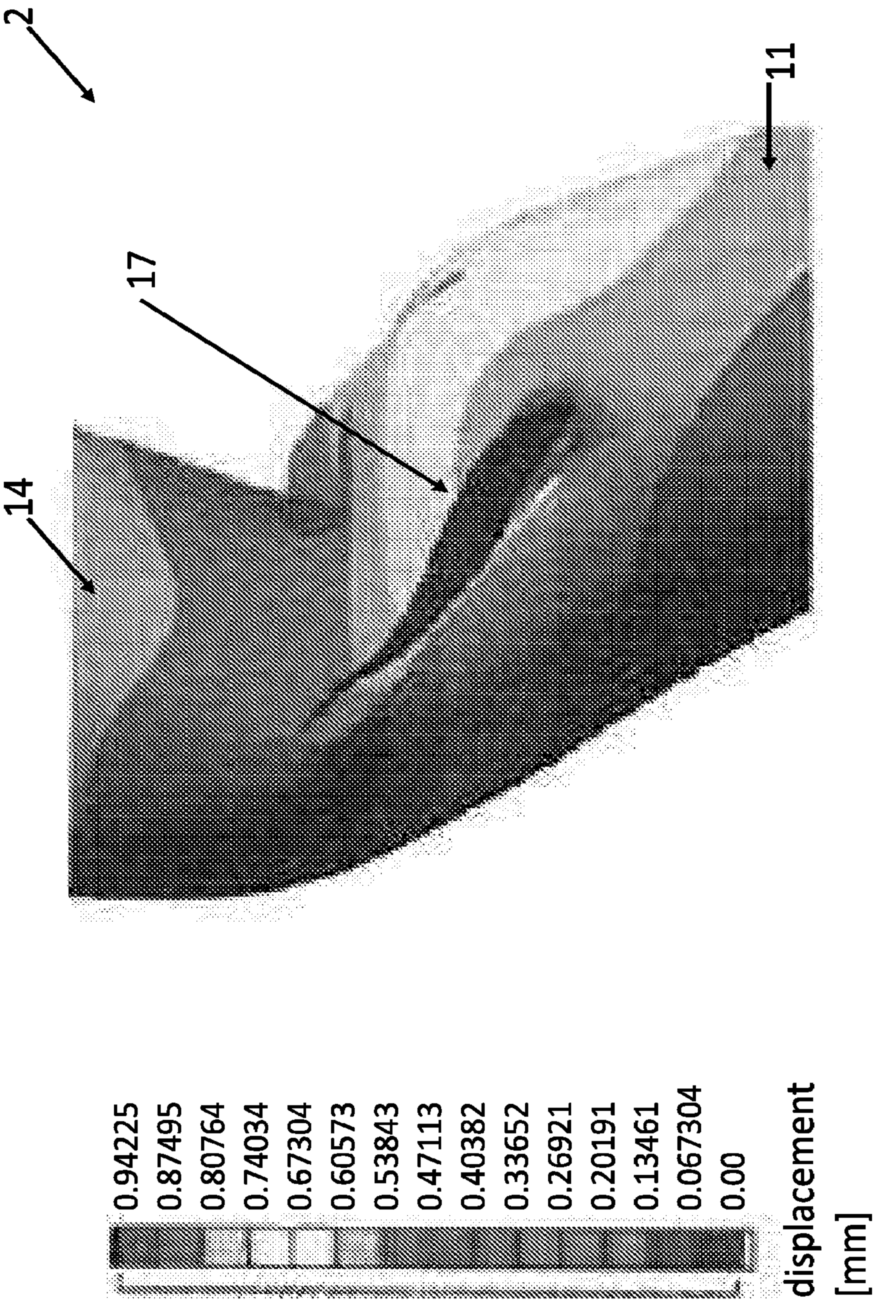
FIG. 13 shows a finite element modeling result of the cannula embodiment of FIGS. 12A-12D.

FIG. 13 shows a finite element modeling result of the cannula embodiment of FIGS. 12A-12D. FIG. 13 shows the tubular body member 14 of the cannula 2 deflecting about the slits 17 when a force is applied to the distal end 11 of the cannula 2.

Where some of the cannulas disclosed herein comprise two (or more) weakened portions, the weakened portions can be (though they need not be) identical, e.g., each comprising a slit, hole or groove, or they may comprise different configurations, e.g., one comprising a slit or a lateral port and the other comprising a part of the wall made in a softer material and/or being thinner compared to the rest of the wall. In some instances, at least one of the weakened portions is a slit in the wall of the tubular body member.

In some embodiments, at least one of the weakened portions provides an opening between the internal bore and the outside of the cannula, wherein the therapeutic agent (e.g., a drug) may leave the inside of the cannula even in the presence of an obstruction or occlusion. For example, if kinking occurs in a cannula, such kinking may occur within one of the weakened portions of the cannula, allowing the therapeutic agent (e.g., a drug) to be delivered through the other weakened portion(s). Likewise, if the distal tip of the outlet is obstructed, the pressure inside the cannula increases and weakened portions comprising slits, hole or grooves will flex outwards providing larger openings in the wall and through the openings, the fluid will leave.

According to some implementations, the weakened portions are all at the same distance from the distal tip opening. In other embodiments, the weakened portions are about 0.2 to about 2.5 mm from the distal tip opening. In yet other embodiments, the weakened portions are about 0.5 to about 1.5 mm from the distal tip opening, or about 0.75 to about 1.25 mm from the distal tip opening, the weakened portions extending towards the proximal portion of the cannula. In some embodiments, the weakened portions are about 0.2 mm from the tip opening, about 0.4 mm from the tip opening, about 0.6 mm from the tip opening, about 0.8 mm from the tip opening, about 1.0 mm from the tip opening, about 1.2 mm from the tip opening, about 1.4 mm from the tip opening, about 1.6 mm from the tip opening, about 1.8 mm from the tip opening, about 2.0 mm from the tip opening, about 2.2 mm from the tip opening, about 2.4 mm from the tip opening, or about 2.5 mm from the tip opening. In other embodiments, the weakened portions are about 0.25 mm, about 0.5 mm, about 0.75 mm, about 1.0 mm, about 1.25 mm, about 1.5 mm, about 1.75 mm, about 2.0 mm, about 2.25 mm or about 2.5 mm from the tip opening.

According to some embodiments, the weakened portions have an extension in the longitudinal direction parallel with the longitudinal axis of the cannula, the length of the weakened portions being in a range of 0.2-1.5 mm, 0.4-0.8 mm, or 0.4-0.6 mm. In some embodiments, the length of the weakened portions is about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm or about 1.5 mm.

In some embodiments, a longitudinal axis of each weakened portion forms an angle with a longitudinal axis of the cannula, wherein the angle is different from 90°. In some embodiments, a longitudinal axis of each weakened portion forms an angle with a longitudinal axis of the cannula, wherein the angle is substantially 0°. In some embodiments, a longitudinal axis of each weakened portion forms an angle with a longitudinal axis of the cannula, wherein the angle is between 0° and 90°. In other embodiments, a longitudinal axis of each weakened portion forms an angle with a longitudinal axis of the cannula, wherein the angle is 0°, 10°, 20°, 30°, 40°, 50°, 60°, 70°, 80° or 90°.

In some embodiments, the weakened portions are each formed as a slit and formed at the same circumferential location of the tubular body. In other embodiments, the weakened portions comprise 2-10 slits, (e.g., 2-8 slits), and formed at the same circumferential location of the tubular body. In other embodiments, the weakened portions comprise 2-6 slits, 2-4 slits or 2 slits.

In some embodiments, of the infusion devices and cannulas disclosed herein, even when the cannula does not kink or the internal pressure does not exceed the pressure at the tip of the cannula, at least one of the slits provides a fluid communication between the internal bore of the cannula and the outside of the cannula.

"Same circumferential location" indicates that the slits are placed in such a way that the upper end of a slit is at the same level as the upper end of the first neighboring slit or between the upper end and the lower end of the first neighboring slit, and the lower end of the slit is at the same level as the lower end of the second neighboring slit or between the upper end and the lower end of the second neighboring slit. By "upper" is meant closest to the proximal portion of the cannula, and by "lower" is meant closest to the distal end or tip of the cannula.

In some embodiments, each weakened portion is formed as a slit and formed at the same circumferential location of the tubular body member, the slits providing slats placed between the slits, the slats are adapted to flex outwards away from the internal bore when the cannula is exposed by compression forces and/or an increased internal pressure. In some embodiments, the slats are delimited by sidewalls parallel to the longitudinal axes of the tubular body member and the sidewalls delimiting each slat are parallel to each other in a radial direction. In some embodiments, the slats are delimited by sidewalls parallel to the longitudinal axis of the tubular body in that the sidewalls for each slat converge in a radial direction towards the outside of the tubular body member, wherein the openings provided by the slits are converging towards the internal bore.

According to some implementations, each of the weakened portions are formed as slits and formed at the same circumferential location of the tubular body member, the slits providing slats between the slits, the slats adapted to flex outwards away from the internal bore when the cannula is exposed to compression forces or when the internal pressure exceeds the pressure at the tip opening. In some embodiments, the bending of the slats may take place substantially in the middle of the slats.

In some embodiments, the slits are formed by laser cutting of a set portion of the tubular implementations, a length of the distal end of the cannula is less than 3.5 mm, less than 3.25 mm, less than 3.0 m, less than 2.75 m, less than 2.5 mm, less than 2.0 mm, less than 1.75 mm, less than 1.5, less than 1.25 mm, or less than 1.5 mm. In some embodiments, a length of the distal end is less than 2.5 mm, and an outer diameter of the distal end is less than 1.5 mm.

In some embodiments, the infusion device is configured for subcutaneous infusion of one or more drugs or other therapeutic agents. According to some implementations, the one or more therapeutic agents comprise insulin.

According to some implementations, the weakened portions are positioned below the basal membrane when the cannula is subcutaneously placed.

In some embodiments, the aspects of the present disclosure include a method of administering a therapeutic agent via an infusion device providing a cannula having a tubular body member with a proximal portion, and a distal portion subcutaneously placed when the infusion device is placed on an outside surface of a patients skin, the tubular body member comprising a tubular wall enclosing a longitudinal extending internal bore, the distal portion having a distal end with a tip end comprising at least one tip opening allowing a portion of the therapeutic agent (e.g., a drug) conveyed through the internal bore in the tubular body member to discharge; and a hub part fastened onto the patient's skin via a mounting pad, wherein the cannula comprises at least two slits in the wall, e.g., 2-10 slits or 2-8 slits, and placed in the distal end of the cannula formed at the same circumferential location of the tubular body, the slits provide slats between the slits, and the cannula is exposed to a compression force whereby the tip opening is substantially closed or the cannula is exposed to an increased internal pressure exceeding the pressure at the tip opening, the compression force or increased internal pressure sees to that the slats are flexing outwards away from the bore, whereby at least one slit is opened between two neighboring slats and forming at least one opening through the opening(s) the therapeutic agent (e.g., a drug) is discharged.

In some embodiments, an infusion device comprises: a cannula having a tubular body member with a proximal portion and a distal portion subcutaneously placed when the infusion device is placed on an outside surface of a patients skin, the tubular body member comprising a tubular wall enclosing a longitudinal extending internal bore, the distal portion having a distal end with a tip end comprising at least one tip opening, allowing a portion of the therapeutic agent (e.g., a drug) conveyed through the internal bore in the tubular body member to discharge; and a hub part configured to be fastened onto the patient's skin via a mounting pad. The cannula includes at least two weakened portions in the wall, a first weakened portion and a second weakened portion in the distal end of the cannula and having a compression strength being smaller than the compression strength of the remaining part of the distal portion. The cannula is adapted to flex in an area comprising the weakened portions when the cannula is exposed to a compression force and/or an increased internal pressure taking place inside the longitudinal extending bore, the internal pressure exceeding the pressure at the tip opening. At least one of the weakened portions provides a fluid communication between the internal bore and the outside of the cannula. The weakened portions all are formed as slits and formed at the same circumferential location of the tubular body the slits provide slats between the slits, the slats are adapted to flex outwards away from the internal bore, when the cannula is exposed for compression forces or/and an increased internal pressure.

According to some implementations, the weakened portions are all formed as slits and formed at the same circumferential location of the tubular body. The slits extend in the longitudinal direction parallel with the longitudinal axis of the bore, the length of the slits being in a range of 0.2-1.5 mm, 0.4-0.8 mm, or 0.4-0.6 mm. According to some implementations, the bending of the slats takes place approximately in the middle of the slats.

According to some implementations, the weakened portions comprise 2-10 slits, e.g., 2-8 slits and are formed at the same circumferential location of the tubular body member. According to some implementations, a length of the distal end of the cannula is less than 3.5 mm or, in some cases, even less than 2.5 mm, and an outer diameter of the distal end is less than 1.5 mm. According to some embodiments, the width of the slits is in a range of 10-200 μm, 10-100 μm, or 10-50 μm.

According to some implementations, all the weakened portions are shaped as slits and are offset in axial direction with respect to one another, and the longitudinal axis of each of the slits are all parallel to a longitudinal axis of the cannula.

According to some implementations, all the weakened portions are shaped as slits, each slit comprises an upper boundary/end closest to the proximal portion and an opposite lower boundary/end closest to the tip opening, each of the upper boundaries/ends are placed within the same distance from the tip opening of the cannula, and a longitudinal axis of each of the slits are all parallel to the longitudinal axis of the cannula.

Other implementations are within the scope of the claims. As used herein, as one of ordinary skill in the art would readily appreciate, the examples and embodiments described herein in connection with to a "therapeutic agent," "drug" or "fluid" are equally applicable to therapeutic agents, fluids, drugs, suspensions and other conventional materials suitable for delivery via a cannula.

The specification and drawings are to be regarded in an illustrative rather than a restrictive sense. It will, however, be evident that various modifications and changes may be made thereunto without departing from the broader spirit and scope of the invention as set forth in the claims. Based on the disclosure and teachings provided herein, a person of ordinary skill in the art will appreciate other ways and/or methods to implement the various embodiments.

What is claimed is:

1. An infusion device for subcutaneous delivery of a therapeutic agent to a patient comprising:

a cannula comprising a tubular body member comprising a tubular wall at least partly enclosing a longitudinally-extending internal bore, a distal portion of the tubular body member having a distal tip end comprising at least one tip opening, wherein the tubular wall comprises at least two weakened portions in the tubular wall oriented in a longitudinal direction parallel with the longitudinally-extending internal bore, the at least two weakened portions being capable of allowing the cannula to flex outwards away from the longitudinally-extending internal bore in an area comprising the at least two weakened portions when the cannula is exposed to a compression force or an increased internal pressure; and a hub part configured to be fastened onto the patient's skin via a mounting pad, wherein each of the at least two weakened portions is formed as a slit located at a same circumferential location of the tubular body member, wherein the slits comprise a particular slit and a corresponding slit, wherein the width of the particular slit is greater than the width of the corresponding slit located about 180 degrees opposite from the particular slit.

2. The infusion device of claim 1, wherein the at least two weakened portions result from material properties of the tubular wall.

3. The infusion device of claim 1, wherein when the cannula is exposed to the compression force and/or the increased internal pressure and the internal pressure in the longitudinally-extending internal bore exceeds the internal pressure at the at least one tip opening, at least one of the at least two weakened portions provides a fluid communication between the longitudinally-extending internal bore and the outside of the cannula.

4. The infusion device of claim 1, wherein the at least two weakened portions comprises 2-10 slits, and the slits are formed at the same circumferential location of the tubular body member.

5. The infusion device of claim 1, wherein each slit has a corresponding and respective width in a range of 10-100 μm.

6. The infusion device of claim 1, wherein the slits are offset in an axial direction with respect to one another, wherein a longitudinal axis of each of the slits is parallel to a longitudinal axis of the cannula.

7. The infusion device of claim 1, wherein each slit comprises an upper or proximal boundary closest to a proximal portion of the cannula, and a lower or distal boundary closest to the at least one tip opening, wherein the upper boundaries are at the same distance from the at least one tip opening of the cannula, and longitudinal axes of each of the slits are each parallel to a longitudinal axis of the cannula.

8. The infusion device of claim 1, wherein the device further comprises a pump in fluid connection with a reservoir configured to store medication/drug.

9. The infusion device of claim 1, wherein the width of the particular slit is about twice as large as the width of the corresponding slit located about 180 degrees opposite from the particular slit.

10. The infusion device of claim 1, wherein the at least two weakened portions comprises six slits, a width of at least three of the six slits being about twice as large as a width of a corresponding slit located about 180 degrees about a circumference of the tubular body member.

* * * * *